US008080386B2

(12) United States Patent
Harris et al.

(10) Patent No.: US 8,080,386 B2
(45) Date of Patent: Dec. 20, 2011

(54) POLYPEPTIDES HAVING ENDOGLUCANASE ACTIVITY AND POLYNUCLEOTIDES ENCODING SAME

(75) Inventors: Paul Harris, Carnation, WA (US); Elena Vlasenko, Davis, CA (US); Elizabeth Zaretsky, Reno, NV (US); Marcus Sakari Kauppinen, Smørum (DK)

(73) Assignees: Novozymes, Inc., Davis, CA (US); Novozymes A/S, Bagsvaerd (DK)

( * ) Notice: Subject to any disclaimer, the term of this patent is extended or adjusted under 35 U.S.C. 154(b) by 416 days.

(21) Appl. No.: 12/294,506

(22) PCT Filed: Mar. 30, 2007

(86) PCT No.: PCT/US2007/065639

§ 371 (c)(1), (2), (4) Date: Mar. 10, 2009

(87) PCT Pub. No.: WO2008/057621

PCT Pub. Date: May 15, 2008

(65) Prior Publication Data

US 2011/0185454 A1 Jul. 28, 2011

Related U.S. Application Data

(60) Provisional application No. 60/788,523, filed on Mar. 30, 2006.

(51) Int. Cl.
*C07K 1/00* (2006.01)
*C12Q 1/34* (2006.01)

(52) U.S. Cl. .......................................... 435/18; 530/350

(58) Field of Classification Search .................. 530/350; 435/183

See application file for complete search history.

(56) References Cited

U.S. PATENT DOCUMENTS 4,081,328 A 3/1978 Skinner et al.

FOREIGN PATENT DOCUMENTS

| | | | |
|---|---|---|---|
| WO | WO 96/29397 | | 9/1996 |
| WO | WO/96/29397 | * | 9/1996 |
| WO | WO 2005/074647 | | 8/2005 |
| WO | WO/2005/074647 | * | 8/2005 |

OTHER PUBLICATIONS

Mertz et al., Phylogenetic Analysis of Family 6 Glycoside Hydrolases, Wiley InterScience(www.interscience.wiley.com), Aug. 5, 2005.

Durand et al., Comparative study of cellulases and hemicellulases from four fungi: mesophiles *Trichoderma reesei* and *Penicillium* sp. and thermophiles *Thielavia terrestris* and *Sporotrichum cellulophilum*, Enzyme Microb. Technol., vol. 6, 1984, pp. 175-180.

Sheppard et al., The use of conserved cellulase family-specific sequences to clone cellulase homologue cDNAs from Fusarium oxysporum, Gene, vol. 150, 1994, pp. 163-167.

Kvesitadze et al., Isolation and properties of a thermostable endoglucanase from a thermophilic mutant strain of Thielavia terrestris, Applied Biochemistry and Biotechnology, vol. 50, 1995, pp. 137-144.

* cited by examiner

*Primary Examiner* — Maryam Monshipouri

(74) *Attorney, Agent, or Firm* — Robert L. Starnes

(57) ABSTRACT

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

20 Claims, 11 Drawing Sheets

AGCCCCCCGTTCAGGCACACTTGGCATCAGATCAGCTTAGCAGCGCCTGCACAGCATGAAGCTCTCGCAGTCGGCCGCG
M K L S Q S A A
CTGGCGGCACTCACCGCGACGGCGCTCGCCGCCCCCTCGCCCACGACGCCGCAGGCGCCGAGGCAGGCTTCAGCCGGCT
L A A L T A T A L A A P S P T T P Q A P R Q A S A G
GCTCGTCTGCGGTCACGCTCGACGCCAGCACCAACGTTTGGAAGAAGTACACGCTGCACCCCAACAGCTACTACCGCAA
C S S A V T L D A S T N V W K K Y T L H P N S Y Y R K
GGAGGTTGAGGCCGCGGTGGCGCAGATCTCGGACCCGGACCTCGCCGCCAAGGCCAAGAAGGTGGCCGACGTCGGCACC
E V E A A V A Q I S D P D L A A K A K K V A D V G T
TTCCTGTGGCTCGACTCGATCGAGAACATCGGCAAGCTGGAGCCGGCGATCCAGGACGTGCCCTGCGAGAACATCCTGG
F L W L D S I E N I G K L E P A I Q D V P C E N I L
GCCTGGTCATCTACGACCTGCCGGGCCGCGACTGCGCGGCCAAGGCGTCCAACGGCGAGCTCAAGGTCGGCGAGATCGA
G L V I Y D L P G R D C A A K A S N G E L K V G E I D
CCGCTACAAGACCGAGTACATCGACAGTGAGTGCTGCCCCCCGGGTTCGAGAAGAGCGTGGGGAAAGGGAAAGGGTTG
R Y K T E Y I D
ACTGACTGACACGGCGCACTGCAGAGATCGTGTCGATCCTCAAGGCACACCCCAACACGGCGTTCGCGCTGGTCATCGA
K I V S I L K A H P N T A F A L V I E
GCCGGACTCGCTGCCCAACCTGGTGACCAACAGCAACTTGGACACGTGCTCGAGCAGCGCGTCGGGCTACCGCGAAGGC
P D S L P N L V T N S N L D T C S S S A S G Y R E G
GTGGCTTACGCCCTCAAGAACCTCAACCTGCCCAACGTGATCATGTACCTCGACGCCGGCCACGGCGGCTGGCTCGGCT
V A Y A L K N L N L P N V I M Y L D A G H G G W L G
GGGACGCCAACCTGCAGCCCGGCGCGCAGGAGCTAGCCAAGGCGTACAAGAACGCCGGCTCGCCCAAGCAGCTCCGCGG
W D A N L Q P G A Q E L A K A Y K N A G S P K Q L R G
CTTCTCGACCAACGTGGCCGGCTGGAACTCCTGGTGAGCTTTTTCCATTCCATTTCTTCTTCCTCTTCTCTCTTCGCT
F S T N V A G W N S W
CCCACTCTGCAGCCCCCCCTCCCCAAGCACCCACTGGCGTTCCGGCTTGCTGACTCGGCCTCCCTTTCCCCGGGCACC

Fig. 2A

```
AGGGATCAATCGCCCGGCGAATTCTCCCAGGCGTCCGACGCCAAGTACAACAAGTGCCAGAACGAGAAGATCTACGTCA
    D  Q  S  P  G  E  F  S  Q  A  S  D  A  K  Y  N  K  C  Q  N  E  K  I  Y  V
GCACCTTCGGCTCCGCGCTCCAGTCGGCCGGCATGCCCAACCACGCCATCGTCGACACGGGCCGCAACGGCGTCACCGG
S  T  F  G  S  A  L  Q  S  A  G  M  P  N  H  A  I  V  D  T  G  R  N  G  V  T  G
CCTGCGCAAGGAGTGGGGTGACTGGTGCAACGTCAACGGTGCAGGTTCGTTGTCTTCTTTTTCTCCTCTTTTGTTTGCA
  L  R  K  E  W  G  D  W  C  N  V  N  G  A
CGTCGTGGTCCTTTTCAAGCAGCCGTGTTTGGTTGGGGAGATGGACTCCGGCTGATGTTCTGCTTCCTCTCTAGGCTT
                                                                          G  F
CGGCGTGCGCCCGACGAGCAACACGGGCCTCGAGCTGGCCGACGCGTTCGTGTGGGTCAAGCCCGGCGGCGAGTCGGAC
  G  V  R  P  T  S  N  T  G  L  E  L  A  D  A  F  V  W  V  K  P  G  G  E  S  D
GGCACCAGCGACAGCTCGTCGCCGCGCTACGACAGCTTCTGCGGCAAGGACGACGCCTTCAAGCCCTCGCCCGAGGCCG
 G  T  S  D  S  S  S  P  R  Y  D  S  F  C  G  K  D  D  A  F  K  P  S  P  E  A
GCACCTGGAACGAGGCCTACTTCGAGATGCTGCTCAAGAACGCCGTGCCGTCGTTCTAAGACGGTCCAGCATCATCCGG
G  T  W  N  E  A  Y  F  E  M  L  L  K  N  A  V  P  S  F
```

Fig. 2B

```
ATGAAGTACCTCAACCTCCTCGCAGCTCTCCTCGCCGTCGCTCCTCTCCCTCGCTGCACCCAGCATCGAGGCCAGAC
 M  K  Y  L  N  L  L  A  A  L  L  A  V  A  P  L  S  L  A  A  P  S  I  E  A  R
AGTCGAACGTCAACCCATACATCGGCAAGAGCCCGCTCGTTATTAGGTCGTACGCCCAAAAGCTTGAGGAGACCGTCAG
Q  S  N  V  N  P  Y  I  G  K  S  P  L  V  I  R  S  Y  A  Q  K  L  E  E  T  V  R
GACCTTCCAGCAACGTGGCGACCAGCTCAACGCTGCGAGGACACGGACGGTGCAGAACGTTGCGACTTTCGCCTGGATC
  T  F  Q  Q  R  G  D  Q  L  N  A  A  R  T  R  T  V  Q  N  V  A  T  F  A  W  I
TCGGATACCAATGGTATTGGAGCCATTCGACCTCTCATCCAAGATGCTCTCGCCCAGCAGGCTCGCACTGGACAGAAGG
 S  D  T  N  G  I  G  A  I  R  P  L  I  Q  D  A  L  A  Q  Q  A  R  T  G  Q  K
TCATCGTCCAAATCGTCGTCTACAACCTCCCAGATCGCGACTGCTCTGCCAACGCCTCGACTGGAGAGTTCACCGTAGG
V  I  V  Q  I  V  V  Y  N  L  P  D  R  D  C  S  A  N  A  S  T  G  E  P  T  V  G
AAACGACGGTCTCAACCGATACAAGAACTTTGTCAACACCATCGCCCGCGAGCTCTCGACTGCTGACGCTGACAAGCTC
  N  D  G  L  N  R  Y  K  N  F  V  N  T  I  A  R  E  L  S  T  A  D  A  D  K  L
CACTTTGCCCTCCTCCTCGAACCCGACGCACTTGCCAACCTCGTCACCAACGCGAATGCCCCCAGGTGCCGAATCGCCG
 H  F  A  L  L  L  E  P  D  A  L  A  N  L  V  T  N  A  N  A  P  R  C  R  I  A
CTCCCGCTTACAAGGAGGGTATCGCCTACACCCTCGCCACCTTGTCCAAGCCCAACGTCGACGTCTACATCGACGCCGC
A  P  A  Y  K  E  G  I  A  Y  T  L  A  T  L  S  K  P  N  V  D  V  Y  I  D  A  A
CAACGGTGGCTGGCTCGGCTGGAACGACAACCTCCGCCCCTTCGCCGAACTCTTCAAGGAAGTCTACGACCTCGCCCGC
  N  G  G  W  L  G  W  N  D  N  L  R  P  F  A  E  L  F  K  E  V  Y  D  L  A  R
CGCATCAACCCCAACGCCAAGGTCCGCGGCGTCCCCGTCAACGTCTCCAACTACAACCAGTACCGCGCTGAAGTCCGCG
 R  I  N  P  N  A  K  V  R  G  V  P  V  N  V  S  N  Y  N  Q  Y  R  A  E  V  R
AGCCCTTCACCGAGTGGAAGGACGCCTGGGACGAGAGCCGCTACGTCAACGTCCTCACCCCGCACCTCAACGCCGTCGG
E  P  F  T  E  W  K  D  A  W  D  E  S  R  Y  V  N  V  L  T  P  H  L  N  A  V  G
CTTCTCCGCGCACTTCATCGTTGACCAGGGACGCGGTGGCAAGGGCGGTATCAGGACGGAGTGGGGCCAGTGGTGCAAC
  F  S  A  H  F  I  V  D  Q  G  R  G  G  K  G  G  I  R  T  E  W  G  Q  W  C  N
GTTAGGAACGCTGGGTTCGGTATCAGGCCTACTGCGGATCAGGGCGTGCTCCAGAACCCGAATGTGGATGCGATTGTGT
 V  R  N  A  G  F  G  I  R  P  T  A  D  Q  G  V  L  Q  N  P  N  V  D  A  I  V
GGGTTAAGCCGGGTGGAGAGTCGGATGGCACGAGTGATTTGAACTCGAACAGGTATGATCCTACGTGCAGGAGTCCGGT
W  V  K  P  G  G  E  S  D  G  T  S  D  L  N  S  N  R  Y  D  P  T  C  R  S  P  V
```

Fig. 4A

```
GGCGCATGTTCCCGCTCCTGAGGCTGGCCAGTGGTTCAACGAGTATGTTGTTAACCTCGTTTTGAACGCTAACCCCCCT
  A  H  V  P  A  P  E  A  G  Q  W  F  N  E  Y  V  V  N  L  V  L  N  A  N  P  P
CTTGAGCCTACCTGGTAA 1203
 L  E  P  T  W
```

Fig. 4B

SEQUENCE LISTING

```
<160> NUMBER OF SEQ ID NOS: 18

<210> SEQ ID NO 1
<211> LENGTH: 1580
<212> TYPE: DNA
<213> ORGANISM: Thielavia terrestris

<400> SEQUENCE: 1

agcccccgt tcaggcacac ttggcatcag atcagcttag cagcgcctgc acagcatgaa      60

gctctcgcag tcggccgcgc tggcggcact caccgcgacg gcgctcgccg ccccctcgcc     120

cacgacgccg caggcgccga ggcaggcttc agccggctgc tcgtctgcgg tcacgctcga     180
```

```
cgccagcacc aacgtttgga agaagtacac gctgcacccc aacagctact accgcaagga    240

ggttgaggcc gcggtggcgc agatctcgga cccggacctc gccgccaagg ccaagaaggt    300

ggccgacgtc ggcaccttcc tgtggctcga ctcgatcgag aacatcggca agctggagcc    360

ggcgatccag gacgtgccct gcgagaacat cctgggcctg gtcatctacg acctgccggg    420

ccgcgactgc gcggccaagg cgtccaacgg cgagctcaag gtcggcgaga tcgaccgcta    480

caagaccgag tacatcgaca gtgagtgctg ccccccgggt tcgagaagag cgtgggggaa    540

agggaaaggg ttgactgact gacacggcgc actgcagaga tcgtgtcgat cctcaaggca    600

caccccaaca cggcgttcgc gctggtcatc gagccggact cgctgcccaa cctggtgacc    660

aacagcaact tggacacgtg ctcgagcagc gcgtcgggct accgcgaagg cgtggcttac    720

gccctcaaga acctcaacct gcccaacgtg atcatgtacc tcgacgccgg ccacggcggc    780

tggctcggct gggacgccaa cctgcagccc ggcgcgcagg agctagccaa ggcgtacaag    840

aacgccggct cgcccaagca gctccgcggc ttctcgacca acgtggccgg ctggaactcc    900

tggtgagctt ttttccattc catttcttct tcctcttctc tcttcgctcc cactctgcag    960

cccccctcc cccaagcacc cactggcgtt ccggcttgct gactcggcct ccctttcccc   1020

gggcaccagg gatcaatcgc ccggcgaatt ctcccaggcg tccgacgcca agtacaacaa   1080

gtgccagaac gagaagatct acgtcagcac cttcggctcc gcgctccagt cggccggcat   1140

gcccaaccac gccatcgtcg acacgggccg caacggcgtc accggcctgc gcaaggagtg   1200

ggtgactgg tgcaacgtca acggtgcagg ttcgttgtct tctttttctc ctcttttgtt   1260

tgcacgtcgt ggtccttttc aagcagccgt gtttggttgg gggagatgga ctccggctga   1320

tgttctgctt cctctctagg cttcggcgtg cgcccgacga gcaacacggg cctcgagctg   1380

gccgacgcgt tcgtgtgggt caagcccggc ggcgagtcgg acggcaccag cgacagctcg   1440

tcgccgcgct acgacagctt ctgcggcaag gacgacgcct tcaagccctc gcccgaggcc   1500

ggcacctgga acgaggccta cttcgagatg ctgctcaaga acgccgtgcc gtcgttctaa   1560

gacggtccag catcatccgg                                                1580
```

<210> SEQ ID NO 2
<211> LENGTH: 396
<212> TYPE: PRT
<213> ORGANISM: Thielavia terrestris

<400> SEQUENCE: 2

```
Met Lys Leu Ser Gln Ser Ala Ala Leu Ala Ala Leu Thr Ala Thr Ala
1               5                   10                  15

Leu Ala Ala Pro Ser Pro Thr Thr Pro Gln Ala Pro Arg Gln Ala Ser
            20                  25                  30

Ala Gly Cys Ser Ser Ala Val Thr Leu Asp Ala Ser Thr Asn Val Trp
        35                  40                  45

Lys Lys Tyr Thr Leu His Pro Asn Ser Tyr Tyr Arg Lys Glu Val Glu
    50                  55                  60

Ala Ala Val Ala Gln Ile Ser Asp Pro Asp Leu Ala Ala Lys Ala Lys
65                  70                  75                  80

Lys Val Ala Asp Val Gly Thr Phe Leu Trp Leu Asp Ser Ile Glu Asn
                85                  90                  95

Ile Gly Lys Leu Glu Pro Ala Ile Gln Asp Val Pro Cys Glu Asn Ile
            100                 105                 110

Leu Gly Leu Val Ile Tyr Asp Leu Pro Gly Arg Asp Cys Ala Ala Lys
        115                 120                 125
```

```
Ala Ser Asn Gly Glu Leu Lys Val Gly Glu Ile Asp Arg Tyr Lys Thr
    130                 135                 140

Glu Tyr Ile Asp Lys Ile Val Ser Ile Leu Lys Ala His Pro Asn Thr
145                 150                 155                 160

Ala Phe Ala Leu Val Ile Glu Pro Asp Ser Leu Pro Asn Leu Val Thr
                165                 170                 175

Asn Ser Asn Leu Asp Thr Cys Ser Ser Ser Ala Ser Gly Tyr Arg Glu
            180                 185                 190

Gly Val Ala Tyr Ala Leu Lys Asn Leu Asn Leu Pro Asn Val Ile Met
        195                 200                 205

Tyr Leu Asp Ala Gly His Gly Gly Trp Leu Gly Trp Asp Ala Asn Leu
    210                 215                 220

Gln Pro Gly Ala Gln Glu Leu Ala Lys Ala Tyr Lys Asn Ala Gly Ser
225                 230                 235                 240

Pro Lys Gln Leu Arg Gly Phe Ser Thr Asn Val Ala Gly Trp Asn Ser
                245                 250                 255

Trp Asp Gln Ser Pro Gly Glu Phe Ser Gln Ala Ser Asp Ala Lys Tyr
            260                 265                 270

Asn Lys Cys Gln Asn Glu Lys Ile Tyr Val Ser Thr Phe Gly Ser Ala
        275                 280                 285

Leu Gln Ser Ala Gly Met Pro Asn His Ala Ile Val Asp Thr Gly Arg
    290                 295                 300

Asn Gly Val Thr Gly Leu Arg Lys Glu Trp Gly Asp Trp Cys Asn Val
305                 310                 315                 320

Asn Gly Ala Gly Phe Gly Val Arg Pro Thr Ser Asn Thr Gly Leu Glu
                325                 330                 335

Leu Ala Asp Ala Phe Val Trp Val Lys Pro Gly Gly Glu Ser Asp Gly
            340                 345                 350

Thr Ser Asp Ser Ser Ser Pro Arg Tyr Asp Ser Phe Cys Gly Lys Asp
        355                 360                 365

Asp Ala Phe Lys Pro Ser Pro Glu Ala Gly Thr Trp Asn Glu Ala Tyr
    370                 375                 380

Phe Glu Met Leu Leu Lys Asn Ala Val Pro Ser Phe
385                 390                 395

<210> SEQ ID NO 3
<211> LENGTH: 1203
<212> TYPE: DNA
<213> ORGANISM: Thielavia terrestris

<400> SEQUENCE: 3

atgaagtacc tcaacctcct cgcagctctc ctcgccgtcg ctcctctctc cctcgctgca      60

cccagcatcg aggccagaca gtcgaacgtc aacccataca tcggcaagag cccgctcgtt     120

attaggtcgt acgcccaaaa gcttgaggag accgtcagga ccttccagca acgtggcgac     180

cagctcaacg ctgcgaggac acggacggtg cagaacgttg cgactttcgc ctggatctcg     240

gataccaatg gtattggagc cattcgacct ctcatccaag atgctctcgc ccagcaggct     300

cgcactggac agaaggtcat cgtccaaatc gtcgtctaca acctcccaga tcgcgactgc     360

tctgccaacg cctcgactgg agagttcacc gtaggaaacg acggtctcaa ccgatacaag     420

aactttgtca acaccatcgc ccgcgagctc tcgactgctg acgctgacaa gctccacttt     480

gccctcctcc tcgaacccga cgcacttgcc aacctcgtca ccaacgcgaa tgcccccagg     540

tgccgaatcg ccgctcccgc ttacaaggag ggtatcgcct acaccctcgc caccttgtcc     600
```

```
aagcccaacg tcgacgtcta catcgacgcc gccaacggtg gctggctcgg ctggaacgac    660

aacctccgcc ccttcgccga actcttcaag gaagtctacg acctcgcccg ccgcatcaac    720

cccaacgcca aggtccgcgg cgtccccgtc aacgtctcca actacaacca gtaccgcgct    780

gaagtccgcg agcccttcac cgagtggaag gacgcctggg acgagagccg ctacgtcaac    840

gtcctcaccc cgcacctcaa cgccgtcggc ttctccgcgc acttcatcgt tgaccaggga    900

cgcggtggca agggcggtat caggacggag tggggccagt ggtgcaacgt taggaacgct    960

gggttcggta tcaggcctac tgcggatcag ggcgtgctcc agaacccgaa tgtggatgcg   1020

attgtgtggg ttaagccggg tggagagtcg gatggcacga gtgatttgaa ctcgaacagg   1080

tatgatccta cgtgcaggag tccggtggcg catgttcccg ctcctgaggc tggccagtgg   1140

ttcaacgagt atgttgttaa cctcgttttg aacgctaacc cccctcttga gcctacctgg   1200

taa                                                                 1203
```

<210> SEQ ID NO 4
<211> LENGTH: 400
<212> TYPE: PRT
<213> ORGANISM: Thielavia terrestris

<400> SEQUENCE: 4

```
Met Lys Tyr Leu Asn Leu Leu Ala Ala Leu Leu Ala Val Ala Pro Leu
1               5                   10                  15

Ser Leu Ala Ala Pro Ser Ile Glu Ala Arg Gln Ser Asn Val Asn Pro
            20                  25                  30

Tyr Ile Gly Lys Ser Pro Leu Val Ile Arg Ser Tyr Ala Gln Lys Leu
        35                  40                  45

Glu Glu Thr Val Arg Thr Phe Gln Gln Arg Gly Asp Gln Leu Asn Ala
    50                  55                  60

Ala Arg Thr Arg Thr Val Gln Asn Val Ala Thr Phe Ala Trp Ile Ser
65                  70                  75                  80

Asp Thr Asn Gly Ile Gly Ala Ile Arg Pro Leu Ile Gln Asp Ala Leu
                85                  90                  95

Ala Gln Gln Ala Arg Thr Gly Gln Lys Val Ile Val Gln Ile Val Val
            100                 105                 110

Tyr Asn Leu Pro Asp Arg Asp Cys Ser Ala Asn Ala Ser Thr Gly Glu
        115                 120                 125

Phe Thr Val Gly Asn Asp Gly Leu Asn Arg Tyr Lys Asn Phe Val Asn
    130                 135                 140

Thr Ile Ala Arg Glu Leu Ser Thr Ala Asp Ala Asp Lys Leu His Phe
145                 150                 155                 160

Ala Leu Leu Leu Glu Pro Asp Ala Leu Ala Asn Leu Val Thr Asn Ala
                165                 170                 175

Asn Ala Pro Arg Cys Arg Ile Ala Ala Pro Ala Tyr Lys Glu Gly Ile
            180                 185                 190

Ala Tyr Thr Leu Ala Thr Leu Ser Lys Pro Asn Val Asp Val Tyr Ile
        195                 200                 205

Asp Ala Ala Asn Gly Gly Trp Leu Gly Trp Asn Asp Asn Leu Arg Pro
    210                 215                 220

Phe Ala Glu Leu Phe Lys Glu Val Tyr Asp Leu Ala Arg Arg Ile Asn
225                 230                 235                 240

Pro Asn Ala Lys Val Arg Gly Val Pro Val Asn Val Ser Asn Tyr Asn
                245                 250                 255

Gln Tyr Arg Ala Glu Val Arg Glu Pro Phe Thr Glu Trp Lys Asp Ala
            260                 265                 270
```

```
Trp Asp Glu Ser Arg Tyr Val Asn Val Leu Thr Pro His Leu Asn Ala
        275                 280                 285

Val Gly Phe Ser Ala His Phe Ile Val Asp Gln Gly Arg Gly Gly Lys
    290                 295                 300

Gly Gly Ile Arg Thr Glu Trp Gly Gln Trp Cys Asn Val Arg Asn Ala
305                 310                 315                 320

Gly Phe Gly Ile Arg Pro Thr Ala Asp Gln Gly Val Leu Gln Asn Pro
                325                 330                 335

Asn Val Asp Ala Ile Val Trp Val Lys Pro Gly Gly Glu Ser Asp Gly
            340                 345                 350

Thr Ser Asp Leu Asn Ser Asn Arg Tyr Asp Pro Thr Cys Arg Ser Pro
        355                 360                 365

Val Ala His Val Pro Ala Pro Glu Ala Gly Gln Trp Phe Asn Glu Tyr
    370                 375                 380

Val Val Asn Leu Val Leu Asn Ala Asn Pro Pro Leu Glu Pro Thr Trp
385                 390                 395                 400


<210> SEQ ID NO 5
<211> LENGTH: 28
<212> TYPE: DNA
<213> ORGANISM: Thielavia terrestris
<220> FEATURE:
<221> NAME/KEY: misc_feature
<222> LOCATION: (17)..(17)
<223> OTHER INFORMATION: N=A,C,G, OR T
<220> FEATURE:
<221> NAME/KEY: misc_feature
<222> LOCATION: (20)..(20)
<223> OTHER INFORMATION: Y=T OR C
<220> FEATURE:
<221> NAME/KEY: misc_feature
<222> LOCATION: (26)..(26)
<223> OTHER INFORMATION: N=A,C,G, OR T

<400> SEQUENCE: 5

agcccgactc cctggcnaay ctggtnac                                          28


<210> SEQ ID NO 6
<211> LENGTH: 24
<212> TYPE: DNA
<213> ORGANISM: Thielavia terrestris
<220> FEATURE:
<221> NAME/KEY: misc_feature
<222> LOCATION: (13)..(13)
<223> OTHER INFORMATION: N=A,C,G, OR T
<220> FEATURE:
<221> NAME/KEY: misc_feature
<222> LOCATION: (16)..(16)
<223> OTHER INFORMATION: Y=T OR C
<220> FEATURE:
<221> NAME/KEY: misc_feature
<222> LOCATION: (19)..(19)
<223> OTHER INFORMATION: N=A,C,G, OR T
<220> FEATURE:
<221> NAME/KEY: misc_feature
<222> LOCATION: (21)..(21)
<223> OTHER INFORMATION: Y=T OR C

<400> SEQUENCE: 6

gcactcgccg ccnggyttna ycca                                              24


<210> SEQ ID NO 7
<211> LENGTH: 25
<212> TYPE: DNA
<213> ORGANISM: Thielavia terrestris

<400> SEQUENCE: 7
```

cttggtaccg agctcggatc cacta 25

<210> SEQ ID NO 8
<211> LENGTH: 25
<212> TYPE: DNA
<213> ORGANISM: Thielavia terrestris

<400> SEQUENCE: 8
atagggcgaa ttgggccctc tagat 25

<210> SEQ ID NO 9
<211> LENGTH: 12
<212> TYPE: DNA
<213> ORGANISM: Thielavia terrestris

<400> SEQUENCE: 9
ctttccagca ca 12

<210> SEQ ID NO 10
<211> LENGTH: 22
<212> TYPE: DNA
<213> ORGANISM: Aspergillus nidulans

<400> SEQUENCE: 10
gtgccccatg atacgcctcc gg 22

<210> SEQ ID NO 11
<211> LENGTH: 26
<212> TYPE: DNA
<213> ORGANISM: Aspergillus nidulans

<400> SEQUENCE: 11
gagtcgtatt tccaaggctc ctgacc 26

<210> SEQ ID NO 12
<211> LENGTH: 24
<212> TYPE: DNA
<213> ORGANISM: Aspergillus nidulans

<400> SEQUENCE: 12
ggaggccatg aagtggacca acgg 24

<210> SEQ ID NO 13
<211> LENGTH: 45
<212> TYPE: DNA
<213> ORGANISM: Aspergillus niger

<400> SEQUENCE: 13
caccgtgaaa gccatgctct ttccttcgtg tagaagacca gacag 45

<210> SEQ ID NO 14
<211> LENGTH: 45
<212> TYPE: DNA
<213> ORGANISM: Aspergillus niger

<400> SEQUENCE: 14
ctggtcttct acacgaagga aagagcatgg ctttcacggt gtctg 45

<210> SEQ ID NO 15
<211> LENGTH: 44
<212> TYPE: DNA
<213> ORGANISM: Aspergillus niger

<400> SEQUENCE: 15

-continued

```
ctatatacac aactggattt accatgggcc cgcggccgca gatc                    44


<210> SEQ ID NO 16
<211> LENGTH: 44
<212> TYPE: DNA
<213> ORGANISM: Aspergillus niger

<400> SEQUENCE: 16

gatctgcggc cgcgggccca tggtaaatcc agttgtgtat atag                    44


<210> SEQ ID NO 17
<211> LENGTH: 29
<212> TYPE: DNA
<213> ORGANISM: Thielavia terrestris

<400> SEQUENCE: 17

actggattac catgaagctc tcgcagtcg                                     29


<210> SEQ ID NO 18
<211> LENGTH: 30
<212> TYPE: DNA
<213> ORGANISM: Thielavia terrestris

<400> SEQUENCE: 18

agtcacctct agttagaacg acggcacggc                                    30
```

POLYPEPTIDES HAVING ENDOGLUCANASE ACTIVITY AND POLYNUCLEOTIDES ENCODING SAME

CROSS-REFERENCE TO RELATED APPLICATIONS

This application is a 35 U.S.C. 371 national application of PCT/US07/65639 filed on Mar, 30, 2007 and claims priority from U.S. provisional application Ser. No. 60/788,523 filed on Mar. 30, 2006, which applications are fully incorporated herein by reference.

BACKGROUND OF THE INVENTION

1. Field of the Invention

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiohydrolase I is a 1,4-D-glucan cellobiohydrolase (EC. 3.2.1.91) activity which catalyzes the hydrolysis of 1,4-beta-D-glucosidic linkages in cellulose, cellotetriose, or any beta-1,4-linked glucose containing polymer, releasing cellobiose from the reducing ends of the chain. Cellobiohydrolase II is a 1,4-D-glucan cellobiohydrolase (E.C. 3.2.1.91) activity which catalyzes the hydrolysis of 1,4-beta-D-glucosidic linkages in cellulose, cellotetriose, or any beta-1,4-linked glucose containing polymer, releasing cellobiose from the non-reducing ends of the chain. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

Kvesitadaze et al., 1995, *Applied Biochemistry and Biotechnology* 50: 137-143, describe the isolation and properties of a thermostable endoglucanase from a thermophilic mutant strain of *Thielavia terrestris*. Gilbert et al., 1992, *Bioresource Technology* 39: 147-154, describe the characterization of the enzymes present in the cellulose system of *Thielavia terrestris* 255B. Breuil et al., 1986, *Biotechnology Letters* 8: 673-676, describe production and localization of cellulases and beta-glucosidases from *Thielavia terrestris* strains C464 and NRRL 8126.

It would be an advantage in the art to identify new endoglucanases having improved properties.

It is an object of the present invention to provide improved polypeptides having endoglucanase activity and polynucleotides encoding the polypeptides.

SUMMARY OF THE INVENTION

The present invention relates to isolated polypeptides having endoglucanase activity selected from the group consisting of:

(a) a polypeptide comprising an amino acid sequence which has at least 90% identity with the mature polypeptide of SEQ ID NO: 2 or at least 60% identity with the mature polypeptide of SEQ ID NO: 4;

(b) a polypeptide which is encoded by a polynucleotide which hybridizes under at least high stringency conditions with (i) the mature polypeptide coding sequence of SEQ ID NO: 1, (ii) the cDNA sequence contained in the mature polypeptide coding sequence of SEQ ID NO: 1, or (iii) a complementary strand of (i) or (ii), or under at least medium stringency conditions with (i) the mature polypeptide coding sequence of SEQ ID NO: 3, (ii) the genomic DNA sequence comprising the mature polypeptide coding sequence of SEQ ID NO: 3, or (iii) a complementary strand of (i) or (ii); and (c) a variant comprising a conservative substitution, deletion, and/or insertion of one or more amino acids of the mature polypeptide of SEQ ID NO: 2 or SEQ ID NO: 4.

The present invention also relates to isolated polynucleotides encoding polypeptides having endoglucanase activity, selected from the group consisting of:

(a) a polynucleotide encoding a polypeptide comprising an amino acid sequence which has at least 90% identity with the mature polypeptide of SEQ ID NO: 2 or at least 60% identity with the mature polypeptide of SEQ ID NO: 4;

(b) a polynucleotide having at least 90% identity with the mature polypeptide coding sequence of SEQ ID NO: 1 or having at least 60% identity with the mature polypeptide coding sequence of SEQ ID NO: 3; and (c) a polynucleotide which hybridizes under at least high stringency conditions with (i) the mature polypeptide coding sequence of SEQ ID NO: 1, (ii) the cDNA sequence contained in the mature polypeptide coding sequence of SEQ ID NO: 1, or (iii) a complementary strand of (i) or (ii), or under at least medium stringency conditions with (i) the mature polypeptide coding sequence of SEQ ID NO: 3, (ii) the genomic DNA sequence comprising the mature polypeptide coding sequence of SEQ ID NO: 3, or (iii) a complementary strand of (i) or (ii).

In a preferred aspect, the mature polypeptide is amino acids 19 to 396 of SEQ ID NO: 2. In another preferred aspect, the mature polypeptide is amino acids 20 to 400 of SEQ ID NO: 4. In another preferred aspect, the mature polypeptide coding sequence is nucleotides 110 to 1557 of SEQ ID NO: 1. In another preferred aspect, the mature polypeptide coding sequence is nucleotides 58 to 1200 of SEQ ID NO: 3.

The present invention also relates to nucleic acid constructs, recombinant expression vectors, and recombinant host cells comprising the polynucleotides.

The present invention also relates to methods for producing such a polypeptide having endoglucanase activity comprising: (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the polypeptides having endoglucanase activity in detergents and in the conversion of cellulose to glucose.

The present invention further relates to nucleic acid constructs comprising a gene encoding a protein, wherein the gene is operably linked to a nucleotide sequence encoding a signal peptide comprising or consisting of amino acids 1 to 18 of SEQ ID NO: 2 or amino acids 1 to 19 SEQ ID NO: 4, wherein the gene is foreign to the nucleotide sequence.

BRIEF DESCRIPTION OF THE FIGURES

FIGS. 2A and 2B show the genomic DNA sequence and the deduced amino acid sequence of a *Thielavia terrestris* NRRL 8126 CEL6B endoglucanase (SEQ ID NOs: 1 and 2, respectively).

FIGS. 4A and 4B show the cDNA sequence and the deduced amino acid sequence of a *Thielavia terrestris* NRRL 8126 CEL6C endoglucanase (SEQ ID NOs: 3 and 4, respectively).

DEFINITIONS

Figure 1:
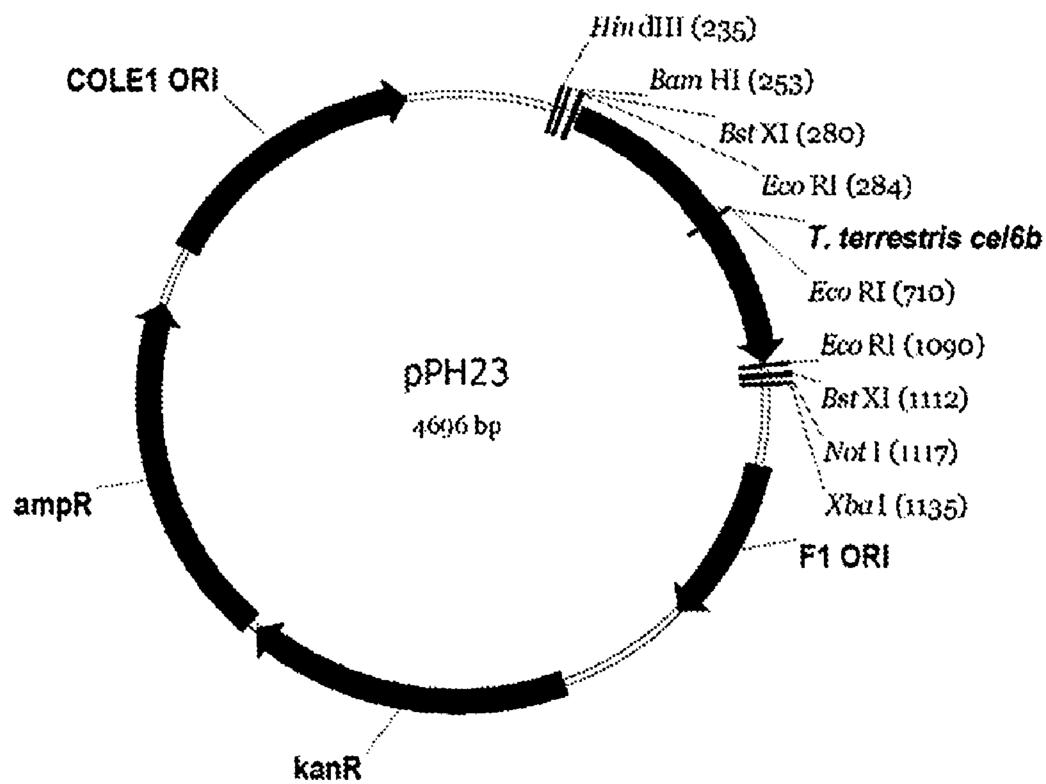
FIG. 1 shows a restriction map of pPH23.

Endoglucanase activity: The term "endoglucanase activity" is defined herein as an endo-1,4-beta-D-glucan 4-glucanohydrolase (E.C. No. 3.2.1.4) which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268. One unit of endoglucanase activity is defined as 1.0 μmole of reducing sugars produced per minute at 50° C., pH 4.8.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the endoglucanase activity of the polypeptide consisting of the amino acid sequence shown as amino acids 18 to 336 of SEQ ID NO: 2.

Family 6 glycoside hydrolase or Family GH6: The term "Family 6 glycoside hydrolase" or "Family GH6" is defined herein as a polypeptide falling into the glycoside hydrolase Family 6 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Mature polypeptide: The term "mature polypeptide" is defined herein as a polypeptide having endoglucanase activity that is in its final form following translation and any post-translational modifications, such as N-terminal processing, C-terminal truncation, glycosylation, etc.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The output of Needle labeled "longest identity" is used as the percent identity and is calculated as follows:

$$(\text{Identical Residues} \times 100)/(\text{Length of Alignment} - \text{Number of Gaps in Alignment})$$

For purposes of the present invention, the degree of identity between two nucleotide sequences is determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EDNAFULL matrix. The output of Needle labeled "longest identity" is used as the percent identity and is calculated as follows:

$$(\text{Identical Residues} \times 100)/(\text{Length of Alignment} - \text{Number of Gaps in Alignment})$$

Homologous sequence: The term "homologous sequence" is defined herein as a predicted protein which gives an E value (or expectancy score) of less than 0.001 in a fasta search (Pearson, W. R., 1999, in *Bioinformatics Methods and Protocols*, S. Misener and S. A. Krawetz, ed., pp. 185-219) with SEQ ID NO: 2 or SEQ ID NO: 4.

Polypeptide fragment: The term "polypeptide fragment" is defined herein as a polypeptide having one or more amino acids deleted from the amino and/or carboxyl terminus of the mature polypeptide of SEQ ID NO: 2 or SEQ ID NO: 4; or a homologous sequence thereof; wherein the fragment has endoglucanase activity. In a preferred aspect, a fragment contains at least 320 amino acid residues, more preferably at least 340 amino acid residues, and most preferably at least 360 amino acid residues of the mature polypeptide of SEQ ID NO: 2 or a homologous sequence thereof. In another preferred aspect, a fragment contains at least 320 amino acid residues, more preferably at least 340 amino acid residues, and most preferably at least 360 amino acid residues of the mature polypeptide of SEQ ID NO: 4 or a homologous sequence thereof.

Subsequence: The term "subsequence" is defined herein as a nucleotide sequence having one or more nucleotides deleted from the 5' and/or 3' end of the mature polypeptide coding sequence of SEQ ID NO: 1; or a homologous sequence thereof; wherein the subsequence encodes a polypeptide fragment having endoglucanase activity. In a preferred aspect, a subsequence contains at least 960 nucleotides, more preferably at least 1020 nucleotides, and most preferably at least 1080 nucleotides of the mature polypeptide coding sequence of SEQ ID NO: 1 or a homologous sequence thereof. In another preferred aspect, a subsequence contains at least 960 nucleotides, more preferably at least 1020 nucleotides, and most preferably at least 1080 nucleotides of the mature polypeptide coding sequence of SEQ ID NO: 3 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form". The polynucleotides may be of genomic, cDNA, RNA, semisynthetic, synthetic origin, or any combinations thereof.

Mature polypeptide coding sequence: The term "mature polypeptide coding sequence" is defined herein as a nucleotide sequence that encodes a mature polypeptide having endoglucanase activity.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2 or SEQ ID NO: 4; or a homologous sequence thereof; as well as genetic manipulation of the DNA encoding such a polypeptide. The modification can be substitutions, deletions and/or insertions of one or more amino acids as well as replacements of one or more amino acid side chains.

Artificial variant: When used herein, the term "artificial variant" means a polypeptide having endoglucanase activity produced by an organism expressing a modified nucleotide sequence of the mature polypeptide coding sequence of SEQ ID NO: 1 or SEQ ID NO: 3; or a homologous sequence thereof. The modified nucleotide sequence is obtained through human intervention by modification of the nucleotide sequence disclosed in SEQ ID NO: 1 or SEQ ID NO: 3; or a homologous sequence thereof.

DETAILED DESCRIPTION OF THE INVENTION

Polypeptides Having Endoglucanase Activity

In a first aspect, the present invention relates to isolated polypeptides comprising an amino acid sequence which has a degree of identity to the mature polypeptide of SEQ ID NO: 2 or SEQ ID NO: 4, of at least 60%, preferably at least 65%, more preferably at least 70%, more preferably at least 75%, more preferably at least 80%, more preferably at least 85%, even more preferably at least 90%, most preferably at least 95%, and even most preferably at least 97%, 98%, or 99%, which have endoglucanase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from the mature polypeptide of SEQ ID NO: 2 or SEQ ID NO: 4.

A polypeptide of the present invention preferably comprises the amino acid sequence of SEQ ID NO: 2 or an allelic variant thereof; or a fragment thereof that has endoglucanase activity. In a preferred aspect, a polypeptide comprises the amino acid sequence of SEQ ID NO: 2. In another preferred aspect, a polypeptide comprises the mature polypeptide of SEQ ID NO: 2. In another preferred aspect, a polypeptide comprises amino acids 19 to 396 of SEQ ID NO: 2, or an allelic variant thereof; or a fragment thereof that has endoglucanase activity. In another preferred aspect, a polypeptide comprises amino acids 19 to 396 of SEQ ID NO: 2. In another preferred aspect, a polypeptide consists of the amino acid sequence of SEQ ID NO: 2 or an allelic variant thereof; or a fragment thereof that has endoglucanase activity. In another preferred aspect, a polypeptide consists of the amino acid sequence of SEQ ID NO: 2. In another preferred aspect, a polypeptide consists of the mature polypeptide of SEQ ID NO: 2. In another preferred aspect, a polypeptide consists of amino acids 19 to 396 of SEQ ID NO: 2 or an allelic variant thereof; or a fragment thereof that has endoglucanase activity. In another preferred aspect, a polypeptide consists of amino acids 19 to 396 of SEQ ID NO: 2.

A polypeptide of the present invention preferably also comprises the amino acid sequence of SEQ ID NO: 4 or an allelic variant thereof; or a fragment thereof that has endoglucanase activity. In a preferred aspect, a polypeptide comprises the amino acid sequence of SEQ ID NO: 4. In another preferred aspect, a polypeptide comprises the mature polypeptide of SEQ ID NO: 4. In another preferred aspect, a polypeptide comprises amino acids 20 to 400 of SEQ ID NO: 4, or an allelic variant thereof; or a fragment thereof that has endoglucanase activity. In another preferred aspect, a polypeptide comprises amino acids 20 to 400 of SEQ ID NO: 4. In another preferred aspect, a polypeptide consists of the amino acid sequence of SEQ ID NO: 4 or an allelic variant thereof; or a fragment thereof that has endoglucanase activity. In another preferred aspect, a polypeptide consists of the amino acid sequence of SEQ ID NO: 4. In another preferred aspect, a polypeptide consists of the mature polypeptide of SEQ ID NO: 4. In another preferred aspect, a polypeptide consists of amino acids 20 to 400 of SEQ ID NO: 4 or an allelic variant thereof; or a fragment thereof that has endoglucanase activity. In another preferred aspect, a polypeptide consists of amino acids 20 to 400 of SEQ ID NO: 4.

In a second aspect, the present invention relates to isolated polypeptides having endoglucanase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, (iii) a subsequence of (i) or (ii), or (iv) a complementary strand of (i), (ii), or (iii), or with (i) the mature polypeptide coding sequence of SEQ ID NO: 3, (ii) the genomic DNA sequence comprising the mature polypeptide coding sequence of SEQ ID NO: 3, (iii) a subsequence of (i) or (ii), or (iv) a complementary strand of (i), (ii), or (iii) (J. Sambrook, E. F. Fritsch, and T. Maniatis, 1989*, Molecular Cloning, A Laboratory Manual,* 2d edition, Cold Spring Harbor, N.Y.). A subsequence of the mature polypeptide coding sequence of SEQ ID NO: 1 or SEQ ID NO: 3 contains at least 100 contiguous nucleotides or preferably at least 200 contiguous nucleotides. Moreover, the subsequence may encode a polypeptide fragment which has endoglucanase activity. In a preferred aspect, the mature polypeptide coding sequence is nucleotides 110 to 1557 of SEQ ID NO: 1. In another preferred aspect, the mature polypeptide coding sequence is nucleotides 58 to 1200 of SEQ ID NO: 3.

The nucleotide sequence of SEQ ID NO: 1 or SEQ ID NO: 3; or a subsequence thereof; as well as the amino acid sequence of SEQ ID NO: 2 or SEQ ID NO: 4; or a fragment thereof; may be used to design a nucleic acid probe to identify and clone DNA encoding polypeptides having endoglucanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having endoglucanase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or SEQ ID NO: 3; or a subsequence thereof; the carrier material is used in a Southern blot.

For purposes of the present invention, hybridization indicates that the nucleotide sequence hybridizes to a labeled nucleic acid probe corresponding to the mature polypeptide coding sequence of SEQ ID NO: 1 or SEQ ID NO: 3, the cDNA sequence contained in the mature polypeptide coding sequence of SEQ ID NO: 1 or SEQ ID NO: 3; its complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 110 to 1557 of SEQ ID NO: 1. In another preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pPH47 which is contained in *E. coli* NRRL B-30898, wherein the polynucleotide sequence thereof encodes a polypeptide having endoglucanase activity. In another preferred aspect, the nucleic acid probe is the mature polypeptide coding region contained in plasmid pPH47 which is contained in *E. coli* NRRL B-30898.

In another preferred aspect, the nucleic acid probe is the mature polypeptide coding sequence of SEQ ID NO: 3. In another preferred aspect, the nucleic acid probe is nucleotides 58 to 1200 of SEQ ID NO: 3. In another preferred aspect, the nucleic acid probe is a polynucleotide sequence which encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pCIBG146 which is contained in *E. coli* NRRL B-30901, wherein the polynucleotide sequence thereof encodes a polypeptide having endoglucanase activity. In another preferred aspect, the nucleic acid probe is the mature polypeptide coding region contained in plasmid pCIBG146 which is contained in *E. coli* NRRL B-30901.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to artificial variants comprising a conservative substitution, deletion, and/or insertion of one or more amino acids of the mature polypeptide of SEQ ID NO: 2 or SEQ ID NO: 4; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., endoglucanase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2 or SEQ ID NO: 4, such as amino acids 19 to 396 of SEQ ID NO: 2 or amino acids 20 to 400 of SEQ ID NO: 4, is 10, preferably 9, more preferably 8, more preferably 7, more preferably at most 6, more preferably 5, more preferably 4, even more preferably 3, most preferably 2, and even most preferably 1.

Sources of Polypeptides Having Endoglucanase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide having endoglucanase activity, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide having endoglucanase activity; or a *Streptomyces* polypeptide having endoglucanase activity, e.g., a *Streptomyces lividans* or *Streptomyces murinus* polypeptide having endoglucanase activity; or a gram negative bacterial polypeptide having endoglucanase activity, e.g., an *E. coli* or a *Pseudomonas* sp. polypeptide having endoglucanase activity.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces; Schizophyllum, Talaromyces, Thermoascus, Thielavia, Tolypocladium*, or *Trichoderma* polypeptide having endoglucanase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having endoglucanase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide having endoglucanase activity.

In another preferred aspect, the polypeptide is a *Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Thielavia terricola, Thielavia thermophila, Thielavia variospora*, or *Thielavia wareingii* polypeptide having endoglucanase activity.

In a more preferred aspect, the polypeptide is a *Thielavia terrestris* polypeptide, and most preferably *Thielavia terrestris* NRRL 8126, e.g., the polypeptide of SEQ ID NO: 2 or SEQ ID NO: 4, or the mature polypeptide thereof.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides comprising or consisting of a nucleotide sequence which encode a polypeptide of the present invention having endoglucanase activity.

In a preferred aspect, the nucleotide sequence comprises or consists of SEQ ID NO: 1. In another more preferred aspect, the nucleotide sequence comprises or consists of the sequence contained in plasmid pPH47 which is contained in *E. coli* NRRL B-30898. In another preferred aspect, the nucleotide sequence comprises or consists of the mature polypeptide coding region of SEQ ID NO: 1. In another preferred aspect, the nucleotide sequence comprises or consists of nucleotides 110 to 1557 of SEQ ID NO: 1. In another more preferred aspect, the nucleotide sequence comprises or consists of the mature polypeptide coding region contained in plasmid pPH47 which is contained in *E. coli* NRRL B-30898. The present invention also encompasses nucleotide sequences which encode a polypeptide comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 which encode fragments of SEQ ID NO: 2 that have endoglucanase activity.

In another preferred aspect, the nucleotide sequence comprises or consists of SEQ ID NO: 3. In another more preferred aspect, the nucleotide sequence comprises or consists of the sequence contained in plasmid pCIBG146 which is contained in *E. coli* NRRL B-30901. In another preferred aspect, the nucleotide sequence comprises or consists of the mature polypeptide coding region of SEQ ID NO: 3. In another preferred aspect, the nucleotide sequence comprises or consists of nucleotides 58 to 1200 of SEQ ID NO: 3. In another more preferred aspect, the nucleotide sequence comprises or consists of the mature polypeptide coding region contained in plasmid pCIBG146 which is contained in *E. coli* NRRL B-30901.

The present invention also encompasses nucleotide sequences which encode a polypeptide comprising or consisting of the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 which encode fragments of SEQ ID NO: 4 that have endoglucanase activity.

The present invention also relates to mutant polunucleotides comprising or consisting of at least one mutation in the mature polypeptide coding sequence of SEQ ID NO: 1 or the mature polypeptide coding sequence of SEQ ID NO: 3, in which the mutant nucleotide sequence encodes the mature polypeptide of SEQ ID NO: 2 or the mature polypeptide sequence of SEQ ID NO: 4. In a preferred aspect, the mature polypeptide is amino acids 19 to 396 of SEQ ID NO: 2. In another preferred aspect, the mature polypeptide is amino acids 20 to 400 of SEQ ID NO: 4.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to polynucleotides comprising or consisting of nucleotide sequences which have a degree of identity to the mature polypeptide coding sequence of SEQ ID NO: 1 or SEQ ID NO: 3 of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 110 to 1557 of SEQ ID NO: 1. In another preferred aspect, the mature polypeptide coding sequence is nucleotides 58 to 1200 of SEQ ID NO: 3.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1 or SEQ ID NO: 3, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for endoglucanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, supra; Smith et al., 1992, supra; Wlodaver et al., 1992, supra).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1; or (iii) a complementary strand of (i) or (ii), or with (i) the mature polypeptide coding sequence of SEQ ID NO: 3, (ii) the genomic DNA sequence comprising the mature polypeptide coding sequence of SEQ ID NO: 3, or (iii) a complementary strand of (i) or (ii); or allelic variants and subsequences thereof (Sambrook et al., 1989, supra), as defined herein. In a preferred aspect, the mature polypeptide coding sequence of SEQ ID NO: 1 is nucleotides 110 to 1557. In another preferred aspect, the mature polypeptide coding sequence of SEQ ID NO: 3 is nucleotides 58 to 1200.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the cDNA sequence contained in the mature polypeptide coding sequence of SEQ ID NO: 1; or (iii) a complementary strand of (i) or (ii), or with (i) the mature polypeptide coding sequence of SEQ ID NO: 3, (ii) the genomic DNA sequence comprising the mature polypeptide coding sequence of SEQ ID NO: 3, or (iii) a complementary strand of (i) or (ii); and (b) isolating the hybridizing polynucleotide, which encodes a polypeptide having endoglucanase activity. In a preferred aspect, the mature polypeptide coding sequence of SEQ ID NO: 1 is nucleotides 110 to 1557. In another preferred aspect, the mature polypeptide coding sequence of SEQ ID NO: 3 is nucleotides 58 to 1200.

Nucleic Acid Constructs

The present invention also relates to nucleic acid constructs comprising an isolated polynucleotide of the present invention operably linked to one or more control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei lipase, Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens cellulase, Humicola insolens* endoglucanase V, and *Humicola lanuginosa* lipase.

In a preferred aspect, the signal peptide is amino acids 1 to 18 of SEQ ID NO: 2. In another preferred aspect, the signal peptide coding region is nucleotides 56 to 109 of SEQ ID NO: 1 which encode amino acids 1 to 18 of SEQ ID NO: 2.

In another preferred aspect, the signal peptide is amino acids 1 to 19 of SEQ ID NO: 4. In another preferred aspect, the signal peptide coding region is nucleotides 1 to 57 of SEQ ID NO: 3 which encode amino acids 1 to 19 of SEQ ID NO: 4.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus.*

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus.*

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus.*

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizen, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacteria Symposium Series No.* 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising: (a) cultivating a cell, which in its wild-type form is capable of producing the polypeptide, under conditions conducive for production of the polypeptide; and (b) recovering the polypeptide. In a preferred aspect, the cell is of the genus *Thielavia*. In a more preferred aspect, the cell is *Thielavia terrestris*. In a most preferred aspect, the cell is *Thielavia terrestris* NRRL 8126.

The present invention also relates to methods for producing a polypeptide of the present invention, comprising: (a) cultivating a host cell under conditions conducive for production of the polypeptide; and (b) recovering the polypeptide.

The present invention also relates to methods for producing a polypeptide of the present invention, comprising: (a) cultivating a host cell under conditions conducive for production of the polypeptide, wherein the host cell comprises a mutant nucleotide sequence having at least one mutation in the mature polypeptide coding sequence of SEQ ID NO: 1 or SEQ ID NO: 3, wherein the mutant nucleotide sequence encodes a polypeptide which comprises or consists of the mature polypeptide of SEQ ID NO: 2 or SEQ ID NO: 4, and (b) recovering the polypeptide.

In a preferred aspect, the mature polypeptide of SEQ ID NO: 2 is amino acids 19 to 396. In another preferred aspect, the mature polypeptide of SEQ ID NO: 4 is amino acids 20 to 400.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to a transgenic plant, plant part, or plant cell which has been transformed with a nucleotide sequence encoding a polypeptide having endoglucanase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the $^{35}$S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising: (a) cultivating a transgenic plant or a plant cell comprising a polynucleotide encoding a polypeptide having endoglucanase activity of the present invention under conditions conducive for production of the polypeptide; and (b) recovering the polypeptide.

Removal or Reduction of Endoglucanase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising: (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of endoglucanase activity by fermentation of a cell which produces both a polypeptide of the present invention as well as the protein product of interest by adding an effective amount of an agent capable of inhibiting endoglucanase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of endoglucanase activity by cultivating the cell under conditions permitting the expression of the product, subjecting the resultant culture broth to a combined pH and temperature treatment so as to reduce the endoglucanase activity substantially, and recovering the product from the culture broth. Alternatively, the combined pH and temperature treatment may be performed on an enzyme preparation recovered from the culture broth. The combined pH and temperature treatment may optionally be used in combination with a treatment with an endoglucanase inhibitor.

In accordance with this aspect of the invention, it is possible to remove at least 60%, preferably at least 75%, more preferably at least 85%, still more preferably at least 95%, and most preferably at least 99% of the endoglucanase activity. Complete removal of endoglucanase activity may be obtained by use of this method.

The combined pH and temperature treatment is preferably carried out at a pH in the range of 2-3 or 10-11 and a temperature in the range of at least 75-85° C. for a sufficient period of time to attain the desired effect, where typically, 1 to 3 hours is sufficient.

The methods used for cultivation and purification of the product of interest may be performed by methods known in the art.

The methods of the present invention for producing an essentially endoglucanase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The endoglucanase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from endoglucanase activity which is produced by a method of the present invention.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, preferably *Humi-*

*cola insolens* or *Humicola lanuginosa*; or *Trichoderma*, preferably *Trichoderma harzianum, Trichoderma koningii, Trichoderma longibrachiatum, Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having endoglucanase activity, or compositions thereof.

Degradation of Biomass to Monosaccharides, Disaccharides, and Polysaccharides

The polypeptides having endoglucanase activity, and host cells of the present invention may be used in the production of monosaccharides, disaccharides, and polysaccharides as chemical or fermentation feedstocks from biomass for the production of ethanol, plastics, or other products or intermediates. The polypeptides having endoglucanase activity may be in the form of a crude fermentation broth with or without the cells removed or in the form of a semi-purified or purified enzyme preparation. Alternatively, a host cell of the present invention may be used as a source of the polypeptide having endoglucanase activity in a fermentation process with the biomass.

Biomass can include, but is not limited to, wood resources, municipal solid waste, wastepaper, and crop residues (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, *Recent Progress in Bioconversion of Lignocellulosics*, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of glycohydrolases are used to breakdown cellulosic biomass:

(1) The "endo-1,4-beta-glucanases" or 1,4-beta-D-glucan-4-glucanohydrolases (EC 3.2.1.4), which act randomly on soluble and insoluble 1,4-beta-glucan substrates.

(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.

(3) The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically resulting in efficient decrystallization and hydrolysis of native cellulose from biomass to yield reducing sugars.

The polypeptides having endoglucanase activity of the present invention may be used in conjunction with the above-noted enzymes to further degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

Ethanol can be produced by enzymatic degradation of biomass and conversion of the released saccharides to ethanol. This kind of ethanol is often referred to as bioethanol or biofuel. It can be used as a fuel additive or extender in blends of from less than 1% and up to 100% (a fuel substitute).

Detergent Compositions

The polypeptides having endoglucanase activity of the present invention may be added to and thus become a component of a detergent composition.

The detergent composition of the present invention may be, for example, formulated as a hand or machine laundry detergent composition including a laundry additive composition suitable for pre-treatment of stained fabrics and a rinse added fabric softener composition, or formulated as a detergent composition for use in general household hard surface cleaning operations, or formulated for hand or machine dishwashing operations.

In a specific aspect, the present invention provides a detergent additive comprising the polypeptides having endoglucanase activity of the present invention. The detergent additive as well as the detergent composition may comprise one or more other enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the enzymatic components should be compatible with the selected detergent, (i.e., pH-optimum, compatibility with other enzymatic and non-enzymatic ingredients, etc.), and the enzymatic components should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novozymes A/S), Maxatase™

Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta,* 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipases include Lipolase™, Lipolase Ultra™, and Lipex™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, or *Trichoderma* e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluclast®, Celluzyme™, and Carezyme™ (Novozymes A/S), Clazinase™, and Puradax HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The enzymatic component(s) may be included in a detergent composition by adding separate additives containing one or more enzymes, or by adding a combined additive comprising all of these enzymes. A detergent additive of the present invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the present invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system that may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzymatic component(s) of the detergent composition of the present invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzymatic component, in particular the polypeptides having endoglucanase activity of the present invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The polypeptides having endoglucanase activity of the present invention may additionally be incorporated in the detergent formulations disclosed in WO 97/07202 which is hereby incorporated as reference.

Signal Peptides

The present invention also relates to nucleic acid constructs comprising a gene encoding a protein operably linked to a nucleotide sequence encoding a signal peptide comprising or consisting of amino acids 1 to 18 of SEQ ID NO: 2 or amino acids 1 to 19 of SEQ ID NO: 4, wherein the gene is foreign to the nucleotide sequence.

In a preferred aspect, the nucleotide sequence comprises nucleotides 56 to 109 of SEQ ID NO: 1. In another preferred aspect, the nucleotide sequence consists of nucleotides 56 to 109 of SEQ ID NO: 1.

In another preferred aspect, the nucleotide sequence comprises nucleotides 1 to 57 of SEQ ID NO: 3. In another preferred aspect, the nucleotide sequence consists of nucleotides 1 to 57 of SEQ ID NO: 3.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

Strains

*Thielavia terrestris* NRRL 8126 was used as the source of the Family 6 polypeptides having endoglucanase activity. *Saccharomyces cerevisiae* strain W3124 (MATa; ura 3-52; leu 2-3, 112; h is 3-D200; pep 4-1137; prc1::HIS3; prb1::LEU2; cir$^+$) was used for screening of *Thielavia terrestris* NRRL 8126 expression libraries for endoglucanase activity. *Aspergillus oryzae* HowB104 strain (alpha-amylase negative) was used for expression of the *Thielavia terrestris* NRRL 8126 CEL6B polypeptide having endoglucanase activity. *Aspergillus oryzae* JaL250 strain (WO 99/61651) was used for expression of the *Thielavia terrestris* NRRL 8126 CEL6C polypeptide having endoglucanase activity.

Media

YEG medium was composed of 0.5% yeast extract and 2% glucose.

YPD medium was composed of 1% yeast extract, 2% peptone, and filter-sterilized 2% glucose added after autoclaving.

YPM medium was composed of 1% yeast extract, 2% peptone, and filter-sterilized 2% maltodextrin added after autoclaving.

SC-URA medium with galactose was composed per liter of 100 ml of 10× Basal salts, 28 ml of 20% casamino acids without vitamins, 10 ml of 1% tryptophan, 3.6 ml of 5% threonine (filter sterilized, added after autoclaving), and 100 ml of 20% galactose (filter sterilized, added after autoclaving).

SC-URA medium with glucose was composed per liter of 100 ml of 10× Basal salts solution, 28 ml of 20% casamino acids without vitamins, 10 ml of 1% tryptophan, 3.6 ml of 5% threonine (filter sterilized, added after autoclaving), and 100 ml of 20% glucose (filter sterilized, added after autoclaving).

10× Basal salts solution was composed per liter of 75 g of yeast nitrogen base, 113 g of succinic acid, and 68 g of NaOH.

SC-agar was composed per liter of SC-URA medium (with glucose or galactose as indicated) and 20 g of agar.

0.1% AZCL HE cellulose SC agar plates with galactose were composed per liter of SC-URA medium with galactose, 20 g of agar, and 0.1% AZCL HE cellulose (Megazyme, Wicklow, Ireland)

PD medium with cellulose was composed per liter of 24 grams potato dextrose (Difco) and 30 grams Solcafloc (Diacel available from Dicalie-Europe-Nord, Gent, Belgium)

Potato dextrose medium was composed per liter of 39 grams of potato dextrose (Difco).

PDA plates were composed per liter of 39 grams of potato dextrose agar.

MDU2BP medium was composed per liter of 45 g of maltose, 1 g of $MgSO_4.7H_2O$, 1 g of NaCl, 2 g of $K_2SO_4$, 12 g of $KH_2PO_4$, 7 g of yeast extract, 2 g of urea, and 0.5 ml of AMG trace metals solution, pH to 5.0.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

COVE plates were composed per liter of 342.3 g of sucrose, 20 ml of COVE salt solution, 10 ml of 1 M acetamide, 10 ml of 1.5 M $CsCl_2$, and 25 g of Noble agar.

COVE salt solution was composed per liter of 26 g of KCl, 26 g of $MgSO_4.7H_2O$, 76 g of $KH_2PO_4$, and 50 ml of COVE trace metals solution.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

Trace metals solution was composed per liter of 41.2 mg of $FeCl_3.6H_2O$, 11.6 mg of $ZnSO_4.7H_2O$, 5.4 mg of $MnSO_4.H_2O$, 2.0 mg of $CuSO_4.5H_2O$, 0.48 mg of $H_3BO_3$, and 67.2 mg of citric acid.

LB plates were composed per liter of 10 g of tryptone, 5 g of yeast extract, 5 g of sodium chloride, and 15 g of Bacto Agar.

SOC medium was composed of 2% tryptone, 0.5% yeast extract, 10 mM NaCl, 2.5 mM KCl, 10 mM $MgCl_2$, and 10 mM $MgSO_4$, and filter-sterilized glucose to 20 mM, added after autoclaving.

Freezing medium was composed of 60% SOC and 40% glycerol.

2×YT medium was composed per liter of 16 g of tryptone, 10 g of yeast extract, 5 g of NaCl, and 15 g of Bacto agar.

Example 1

*Thielavia terrestris* Genomic DNA Extraction

*Thielavia terrestris* NRRL 8126 was grown in 25 ml of YEG medium at 37° C. and 250 rpm for 24 hours. Mycelia were then collected by filtration through Miracloth™ (Cal-Biochem, La Jolla, Calif., USA) and washed once with 25 ml of 10 mM Tris-1 mM EDTA (TE) buffer. Excess buffer was drained from the mycelia preparation, which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg per ml and the mixture was then incubated at 37° C. for 30 minutes. Proteinase K (200 μg/ml) was added and the tube was incubated an additional one hour at 37° C. Finally, the sample was centrifuged for 15 minutes at 12,000×g, and the supernatant was applied to a Qiaprep 8 manifold (QIAGEN Inc., Valencia, Calif., USA). The columns were washed twice with 1 ml of PB (QIAGEN Inc., Valencia, Calif., USA) and 1 ml of PE (QIAGEN Inc., Valencia, Calif., USA) under vacuum. The isolated DNA was eluted with 100 μl of TE, precipitated with ethanol, washed with 70% ethanol, dried under vacuum, resuspended in TE buffer, and stored at 4° C.

To generate genomic DNA for PCR amplification, *Thielavia terrestris* NRRL 8126 was grown in 50 ml of NNCYP medium supplemented with 1% glucose in a baffled shake flask at 42° C. and 200 rpm for 24 hours. Mycelia were harvested by filtration, washed twice in TE (10 mM Tris-1 mM EDTA), and frozen under liquid nitrogen. A pea-size piece of frozen mycelia was suspended in 0.7 ml of 1% lithium dodecyl sulfate in TE and disrupted by agitation with an equal volume of 0.1 mm zirconia/silica beads (Biospec Products, Inc., Bartlesville, Okla., USA) for 45 seconds in a FastPrep FP120 (ThermoSavant, Holbrook, N.Y., USA). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 μl of 0.1×TE and incubated with 1 μl of DNase-free RNase A at 37° C. for 20 minutes. Ammonium acetate was added to 2.5 M and the DNA was precipitated with 2 volumes of ethanol. The pellet was washed in 70% ethanol, air dried, and resuspended in TE buffer.

Example 2

PCR Amplification of a cel6b Gene Fragment from Genomic DNA

Primers were designed based upon conserved motifs found in other Family 6 glycosyl hydrolases. The specific peptide sequences used for primer design were:

EPDSLANLVT (corresponding to amino acids 167 to 176 of SEQ ID NO: 2)

W[I,V]KPGGE[C,S] (amino acids 343 to 350 of SEQ ID NO: 2)

The CODEHOP strategy was employed (Rose et al., 1998, *Nucleic Acids Res.* 26: 1628-35) to design the following primers:

```
Sense Primer:
5'-AGCCCGACTCCCTGGCNAAYCTGGTNAC-3' (SEQ ID NO: 5)

Antisense Primer:
5'-GCACTCGCCGCCNGGYTTNAYCCA-3'     (SEQ ID NO: 6)
```

PCR amplification was performed in a volume of 30 μl containing 1× AmpliTaq buffer (Applied Biosystems, Foster City, Calif., USA), 2.5 units of AmpliTaq DNA polymerase (Applied Biosystems, Foster City, Calif., USA), 1 μM of each sense and antisense primer, and approximately 1 μg of genomic DNA from *Thielavia terrestris*. Amplification was performed in a Robocycler (Stratagene, La Jolla, Calif., USA) programmed for 1 cycle at 96° C. for 3 minutes and 72° C. for 3 minutes (during which DNA polymerase was added); and 35 cycles each at 94° C. for 45 seconds, at 58° C. for 45 seconds, and at 72° C. for 1 minute; followed by a final extension at 72° C. for 7 minutes.

The reaction products were fractionated on a 1.6% agarose gel using 40 mM Tris base-20 mM sodium acetate-1 mM disodium EDTA (TAE) buffer, and a band of approximately 800 bp was excised, purified using a QIAEX II Gel Extraction Kit (QIAGEN Inc., Valencia, Calif., USA), and subcloned using a TOPO TA Kit (Invitrogen, Carlsbad, Calif., USA).

The plasmid from one *E. coli* transformant was sequenced and found to contain an insert of 789 bp coding for a Family 6 protein (CEL6B). This plasmid was designated pPH23 (FIG. 1).

Example 3

Genomic DNA Library Construction and Screening

A genomic DNA library of *Thielavia terrestris* NRRL 8126 was constructed using the bacteriophage cloning vector λZipLox (Life Technologies, Gaithersburg, Md., USA) with *E. coli* Y1090ZL cells (Life Technologies, Gaithersburg, Md., USA) as a host for plating and purification of recombinant bacteriophage and *E. coli* DH10Bzip (Life Technologies, Gaithersburg, Md., USA) for excision of individual pZL1 clones containing the cel6b gene.

*Thielavia terrestris* NRRL 8126 genomic DNA prepared as described in Example 1 was partially digested with Tsp 5091 and size-fractionated on 1% agarose gels using TAE buffer. DNA fragments migrating in the size range 3-7 kb were excised and eluted from the gel using Prep-a-Gene reagents (BioRad Laboratories, Hercules, Calif., USA). The eluted DNA fragments were ligated with Eco RI-cleaved and dephosphorylated λZipLox vector arms (Life Technologies, Gaithersburg, Md., USA), and the ligation mixtures were packaged using commercial packaging extracts (Stratagene, La Jolla, Calif., USA). The packaged DNA libraries were plated and amplified in *E. coli* Y1090ZL cells. The unamplified genomic DNA library contained $3.1\times10^6$ pfu/ml (background titers with no DNA were $2.0\times10^4$ pfu/ml.

A *Thielavia terrestris* cel6b probe fragment was amplified from pPH23 using primers homologous to the TOPO vector and Herculase DNA Polymerase (Stratagene, La Jolla, Calif., USA), as shown below.

```
5'-CTTGGTACCGAGCTCGGATCCACTA-3'    (SEQ ID NO: 7)

5'-ATAGGGCGAATTGGGCCCTCTAGAT-3'    (SEQ ID NO: 8)
```

Fifty picomoles of each of the primers were used in a PCR reaction containing 10 ng of pPH23, 1× Herculase Amplification Buffer (Stratagene, La Jolla, Calif., USA), 1 μl of 10 mM blend of dATP, dTTP, dGTP, and dCTP, and 2.5 units of Herculase DNA Polymerase in a final volume of 50 μl. Amplification was performed in a Robocycler programmed for 1 cycle at 94° C. for 1 minute; and 20 cycles each at 94° C. for 30 seconds, 55° C. for 30 seconds, and 72° C. for 1 minute. The heat block then went to a 4° C. soak cycle.

The reaction product was isolated on a 1.0% agarose gel using TAE buffer where a 0.8 kb product band was excised from the gel and purified using a QIAquick Gel Extraction Kit (QIAGEN Inc., Valencia, Calif., USA) according to the manufacturer's instructions. Twenty five ng of the fragment was radiolabeled with $^{32}P$ using a Prime It II Kit (Stratagene, La Jolla, Calif., USA).

Approximately 90,000 plaques from the library were screened by plaque-hybridization using the labeled PCR fragment as the probe. The DNA was cross-linked onto membranes (Hybond N+, Amersham, Arlington Heights, Ill., USA) using a UV Stratalinker (Stratagene, La Jolla, Calif., USA). The $^{32}P$-radiolabeled gene fragment was denatured by adding sodium hydroxide to a final concentration of 0.1 M, and added to a hybridization solution containing 6×SSPE, 7% SDS at an activity of approximately $1\times10^6$ cpm per ml of hybridization solution. The mixture was incubated overnight at 65° C. in a shaking water bath. Following incubation, the membranes were washed three times for fifteen minutes in 0.2×SSC with 0.1% SDS at 65° C. The membranes were dried on blotting paper for 15 minutes, wrapped in SaranWrap™, and exposed to X-ray film overnight at 70° C. with intensifying screens (Kodak, Rochester, N.Y., USA).

Based on the production of strong hybridization signals with the cel6b probe described above, several plaques were chosen for further study. The plaques were purified twice in *E. coli* Y1090ZL cells and the inserted genes and pZL1 plasmid were subsequently excised from the λZipLox vector as pZL1-derivatives (D'Alessio et al., 1992, Focus® 14:76) using in vivo excision by infection of *E. coli* DH10BZL cells (Life Technologies, Gaithersburg, Md., USA). The colonies were inoculated into three ml of LB plus 100 μg/ml ampicillin medium and grown overnight at 37° C. Miniprep DNA was prepared from each of these cultures using a BioRobot 9600 (QIAGEN Inc., Valencia, Calif., USA). A clone designated pPH47 was shown by DNA sequencing to contain the full-length gene for cel6b.

The *E. coli* strain PaHa47 containing plasmid pPH47 was deposited with the Agricultural Research Service Patent Culture Collection, Northern Regional Research Center, 1815. University Street, Peoria, Ill., 61604, as NRRL B-30898, with a deposit date of Feb. 23, 2006.

Example 4

Characterization of the *Thielavia terrestris* Genomic Sequence Encoding a CEL6B Polypeptide Having Endoglucanase Activity DNA sequencing of the *Thielavia terrestris* cel6b genomic clone was performed with an Applied Biosystems Model 3700 Automated DNA Sequencer using version 3.1 Big-Dye™ terminator chemistry (Applied Biosystems, Inc., Foster City, Calif., USA) and dGTP chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

A gene model for the *Thielavia terrestris* cel6b genomic DNA sequence was constructed based on similarity to homologous endoglucanase genes from *Fusarium oxysporum* and *Chtysosporium lucknowense* (Accession numbers XP383804 and AAQ38151.1, respectively).

The nucleotide sequence (SEQ ID NO: 1) and deduced amino acid sequence (SEQ ID NO: 2) of the *Thielavia terrestris* cel6b gene are shown in FIG. 2. The coding sequence is 1505 bp including the stop codon and is interrupted by introns of 77, 127 and 110 bp. The encoded predicted protein is 396 amino acids. The coding region (including introns) is 64.9% G+C. Using the SignalP program (Nielsen et al., 1997, *Protein Engineering* 10:1-6), a signal peptide of 18 residues was predicted. The predicted mature protein contains 378 amino acids with a molecular mass of 40.6 kDa and an isoelectric pH of 5.01.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Thielavia terrestris* gene encoding the CEL6B polypeptide having endoglucanase activity shared 85% and 82% identity (excluding gaps) to the deduced amino acid sequences of two Family 6 glycosyl hydrolase proteins from *Chrysosporium lucknowense* and *Neurospora crassa*, respectively (accession numbers AAQ38151 and Q7RXI7, respectively).

Example 5

Cloning and Expression of the *Thielavia terrestris* cDNA Encoding a CEL6C Polypeptide Having Endoglucanase Activity

*Thielavia terrestris* NRRL 8126 was cultivated in 200 ml of PD medium with cellulose at 30° C. for five days at 200 rpm. Mycelia from the shake flask culture were harvested by filtering the contents through a funnel lined with Miracloth™ (CalBiochem, San Diego, Calif., USA). The mycelia were then sandwiched between two Miracloth pieces and blotted dry with absorbent paper towels. The mycelial mass was then transferred to Falcon 1059 plastic centrifuge tubes and frozen in liquid nitrogen. Frozen mycelia were stored in a −80° C. freezer until use.

The extraction of total RNA was performed with guanidinium thiocyanate followed by ultracentrifugation through a 5.7 M CsCl cushion, and isolation of poly(A)+RNA was carried out by oligo(dT)-cellulose affinity chromatography, using the procedures described in WO 94/14953.

Double-stranded cDNA was synthesized from 5 μg of poly (A)+RNA by the RNase H method (Gubler and Hoffman, 1983, *Gene* 25: 263-269, Sambrook et al., 1989, *Molecular cloning: A laboratory manual*, Cold Spring Harbor lab., Cold Spring Harbor, N.Y., USA). The poly(A)$^+$RNA (5 μg in 5 μl of DEPC (0.1% diethylpyrocarbonate)-treated water) was heated at 70° C. for 8 minutes in a pre-siliconized, RNase-free Eppendorf tube, quenched on ice, and combined in a final volume of 50 μl with reverse transcriptase buffer composed of 50 mM Tris-HCl, pH 8.3, 75 mM KCl, 3 mM $MgCl_2$, 10 mM dithiothreitol (DTT) (Bethesda Research Laboratories, Bethesda, Md., USA), 1 mM of dATP, dGTP and dTTP, and 0.5 mM 5-methyl-dCTP (Pharmacia, Uppsala, Sweden), 40 units of human placental ribonuclease inhibitor (RNasin, Promega, Madison, Wis., USA), 1.45 μg of oligo$(dT)_{18}$-Not I primer (Pharmacia, Uppsala, Sweden), and 1000 units of SuperScript II RNase H reverse transcriptase (Bethesda Research Laboratories, Bethesda, Md., USA). First-strand cDNA was synthesized by incubating the reaction mixture at 45° C. for 1 hour. After synthesis, the mRNA:cDNA hybrid mixture was gel filtrated through a MicroSpin S-400 HR spin column (Pharmacia, Uppsala, Sweden) according to the manufacturer's instructions.

After gel filtration, the hybrids were diluted in 250 μl of second strand buffer (20 mM Tris-HCl, pH 7.4, 90 mM KCl, 4.6 mM $MgCl_2$, 10 mM $(NH_4)_2SO_4$, 0.16 mM NAD) containing 200 μM of each dNTP, 60 units of *E. coli* DNA polymerase I (Pharmacia, Uppsala, Sweden), 5.25 units of RNase H (Promega, Madison, Wis., USA), and 15 units of *E. coli* DNA ligase (Boehringer Mannheim, Manheim, Germany). Second strand cDNA synthesis was performed by incubating the reaction tube at 16° C. for 2 hours and an additional 15 minutes at 25° C. The reaction was stopped by addition of EDTA to a final concentration of 20 mM followed by phenol and chloroform extractions.

The double-stranded cDNA was precipitated at −20° C. for 12 hours by addition of 2 volumes of 96% ethanol and 0.2 volume of 10 M ammonium acetate, recovered by centrifugation at 13,000×g, washed in 70% ethanol, dried, and resuspended in 30 μl of Mung bean nuclease buffer (30 mM sodium acetate pH 4.6, 300 mM NaCl, 1 mM $ZnSO_4$, 0.35 mM DTT, 2% glycerol) containing 25 units of Mung bean nuclease (Pharmacia, Uppsala, Sweden). The single-stranded hair-pin DNA was clipped by incubating the reaction at 30° C. for 30 minutes, followed by addition of 70 μl of 10 mM Tris-HCl-1 mM EDTA pH 7.5, phenol extraction, and precipitation with 2 volumes of 96% ethanol and 0.1 volume of 3 M sodium acetate pH 5.2 on ice for 30 minutes.

The double-stranded cDNAs were recovered by centrifugation at 13,000×g and blunt-ended in 30 μl of T4 DNA polymerase buffer (20 mM Tris-acetate, pH 7.9, 10 mM magnesium acetate, 50 mM potassium acetate, 1 mM DTT) containing 0.5 mM of each dNTP and 5 units of T4 DNA polymerase (New England Biolabs, Ipswich, Mass., USA) by incubating the reaction mixture at 16° C. for 1 hour. The reaction was stopped by addition of EDTA to a final concentration of 20 mM, followed by phenol and chloroform extractions, and precipitation for 12 hours at −20° C. by adding 2 volumes of 96% ethanol and 0.1 volume of 3 M sodium acetate pH 5.2.

After the fill-in reaction the cDNAs were recovered by centrifugation at 13,000×g, washed in 70% ethanol, and dried. The cDNA pellet was resuspended in 25 μl of ligation buffer (30 mM Tris-HCl, pH 7.8, 10 mM $MgCl_2$, 10 mM DTT, 0.5 mM ATP) containing 2.5 μg of non-palindromic Bst XI adaptors (Invitrogen, Carlsbad, Calif., USA), shown below, and 30 units of T4 ligase (Promega, Madison, Wis., USA), and then incubated at 16° C. for 12 hours. The reaction was stopped by heating at 65° C. for 20 minutes and then cooled on ice for 5 minutes.

```
5'-CTTTCCAGCACA-3'        (SEQ ID NO: 9)

3'-GAAAGGTC-5'            (SEQ ID NO: 10)
```

The adapted cDNA was digested with Not I, followed by incubation for 2.5 hours at 37° C. The reaction was stopped by heating at 65° C. for 10 minutes. The cDNAs were size-fractionated by gel electrophoresis on a 0.8% SeaPlaque GTG low melting temperature agarose gel (Cambrex Corporation, East Rutherford, N.J., USA) in 44 mM Tris Base, 44 mM boric acid, 0.5 mM EDTA (TBE) buffer to separate unligated adaptors and small cDNAs. The cDNA was size-selected with a cut-off at 0.7 kb and rescued from the gel by use of β-Agarase (New England Biolabs) according to the manufacturer's instructions and precipitated for 12 hours at −20° C. by adding two volumes of 96% ethanol and 0.1 volume of 3 M sodium acetate pH 5.2.

The directional, size-selected cDNA was recovered by centrifugation at 13,000×g, washed in 70% ethanol, dried, and then resuspended in 30 μl of 10 mM Tris-HCl-1 mM EDTA pH 7.5. The cDNAs were desalted by gel filtration through a MicroSpin S-300 HR spin column according to the manufacturer's instructions. Three test ligations were carried out in 10 μl of ligation buffer (30 mM Tris-HCl, pH 7.8, 10 mM $MgCl_2$, 10 mM DTT, 0.5 mM ATP) containing 5 μl of double-stranded cDNA (reaction tubes #1 and #2), 15 units of T4 ligase (Promega, Madison, Wis., USA), and 30 ng (tube #1), 40 ng (tube #2), and 40 ng (tube #3, the vector background control) of Bst XI-Not I cleaved pYES2.0 vector (Invitrogen, Carlsbad, Calif., USA). The ligation reactions were performed by incubation at 16° C. for 12 hours, then heating at 70° C. for 20 minutes, and finally adding 10 μl of water to each tube. One μl of each ligation mixture was electroporated into 40 μl of electrocompetent *E. coli* DH10B cells (Bethesda Research Laboratories, Bethesda, Md., USA) as described by Sambrook et al., 1989, supra.

The *Thielavia terrestris* NRRL 8126 cDNA library was established in *E. coli* DH10B consisting of pools. Each pool was made by spreading transformed *E. coli* on LB ampicillin plates, yielding 15,000-30,000 colonies/plate after incubation at 37° C. for 24 hours. Twenty ml of LB ampicillin medium was added to the plate and the cells were suspended therein. The cell suspension was shaken at 100 rpm in a 50 ml tube for 1 hour at 37° C.

The resulting *Thielavia terrestris* NRRL 8126 cDNA library consisted of approximately $10^6$ individual clones, with a vector background of 1%. Plasmid DNA from some of the library pools was isolated using a Plasmid Midi Kit (QIAGEN Inc., Valencia, Calif., USA) according to the manufacturer's instructions, and stored at −20° C.

One ml aliquots of purified plasmid DNA (100 ng/ml) from some of the library pools (Example 1) were transformed into *Saccharomyces cerevisiae* W3124 by electroporation (Becker and Guarante, 1991, *Methods Enzymol.* 194: 182-187) and the transformants were plated on SC agar containing 2% glucose and incubated at 30° C. In total, 50-100 plates containing 250-400 yeast colonies were obtained from each pool.

After 3-5 days of incubation, the SC agar plates were replica plated onto a set of 0.1% AZCL HE cellulose SC URA agar plates with galactose. The plates were incubated for 2-4 days at 30° C. and endoglucanase positive colonies were identified as colonies surrounded by a blue halo.

Example 6

Characterization of the *Thielavia terrestris* cDNA Sequence Encoding a CEL6C Polypeptide Having Endoglucanase Activity Endoglucanase-expressing yeast colonies were inoculated into 20 ml of YPD medium in 50 ml glass test tubes. The tubes were shaken at 200 rpm for 2 days at 30° C. The cells were harvested by centrifugation for 10 minutes at 3000 rpm in a Heraeus Megafuge 1.0R centrifuge with a 75002252 rotor (Hanau, Germany).

Figure 3:
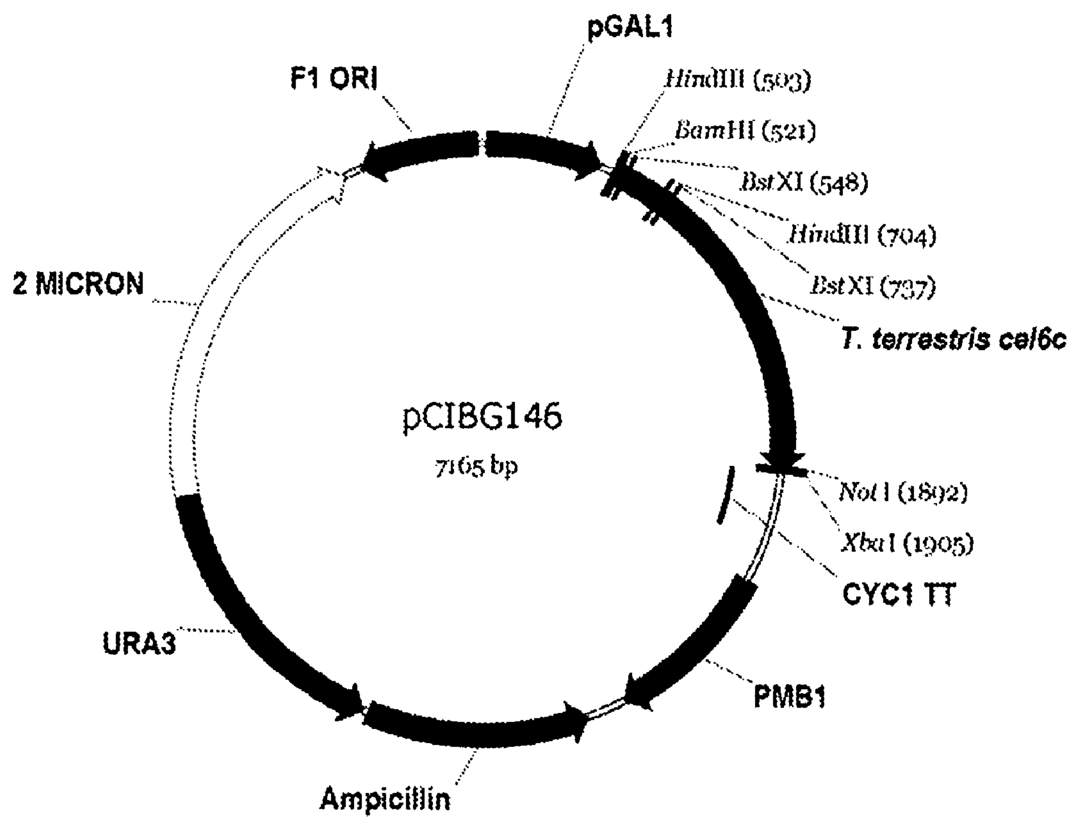
FIG. 3 shows a restriction map of pCIBG146.

DNA was isolated according to WO 94/14953 and dissolved in 50 μl of deionized water. The DNA was transformed into *E. coli* DH10B cells by standard procedures according to Sambrook et al., 1989, supra. One *E. coli* transformant subsequently shown to contain the *Thielavia terrestris* NRRL 8126 cel6c gene was designated pCIBG146 (FIG. 3) and used as material for deposit of biological material. *E. coli* strain pCIBG146 was deposited as *E. coli* NRRL B-30901 on Feb. 23, 2006.

Plasmid DNA was isolated from the *E. coli* transformants using standard procedures according to Sambrook et al., 1989, supra. The full length cDNA sequence of the cel6c gene from *Thielavia terrestris* NRRL 8126 was sequenced with a Tag DyeDeoxy Terminator Cycle Sequencing Kit (Perkin Elmer, Wellesley, Mass., USA) and synthetic oligonucleotide primers using an Applied Biosystems ABI PRISM™ 377 DNA Sequencer (ABI, Foster City, Calif., USA) according to the manufacturer's instructions.

The nucleotide sequence (SEQ ID NO: 3) and deduced amino acid sequence (SEQ ID NO: 4) of the *Thielavia terrestris* cel6c gene are shown in FIG. 4. The coding sequence is 1203 bp including the stop codon. The encoded predicted protein is 400 amino acids. The coding region is 60.0% G+C. Using the SignalP program (Nielsen et al., 1997, supra), a signal peptide of 19 residues was predicted. The predicted mature protein contains 381 amino acids with a molecular mass of 42.1 kDa and pI of 6.76.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* gene encoding the CEL6C polypeptide shared 50%, 49% and 48% identity (excluding gaps) to the deduced amino acid sequences of three Family 6 glycosyl hydrolase proteins from *Neurospora crassa, Magnaporthe grisea*, and *Agaricus bisporus*, respectively (accession numbers Q87B5, XP 368004, and P49075, respectively).

Example 7

Construction of pAILo2 Expression Vector

Expression vector pAILo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). All mutagenesis steps were verified by sequencing using Big-Dye™ terminator chemistry (Applied Biosystems, Inc., Foster City, Calif., USA). Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor™ in vitro Site-Directed Mutagenesis Kit (Promega, Madison, Wis., USA) according to the manufacturer's instructions using the following primers (underlined nucleotide represents the changed base):

```
AMDS3NcoMut (2050):
5'-GTGCCCCATGATACGCCTCCGG-3'        (SEQ ID NO: 11)

AMDS2NcoMut (2721):
5'-GAGTCGTATTTCCAAGGCTCCTGACC-3'    (SEQ ID NO: 12)

AMDS1NcoMut (3396):
5'-GGAGGCCATGAAGTGGACCAACGG-3'      (SEQ ID NO: 13)
```

A plasmid comprising all three expected sequence changes was then submitted to site-directed mutagenesis, using a QuickChange™ Site-Directed Mutagenesis Kit (Stratagene, La Jolla, Calif., USA), to eliminate the Nco I restriction site at the end of the AMG terminator at position 1643. The following primers (underlined nucleotide represents the changed base) were used for mutagenesis:

```
Upper Primer to mutagenize the AMG terminator
sequence:
                                      (SEQ ID NO: 14)
5'-CACCGTGAAAGCCATGCTCTTTCCTTCGTGTAGAAGACCAGAC
AG-3'

Lower Primer to mutagenize the AMG terminator
sequence:
                                      (SEQ ID NO: 15)
5'-CTGGTCTTCTACACGAAGGAAAGAGCATGGCTTTCACGGTGTC
TG-3'
```

Figure 5:
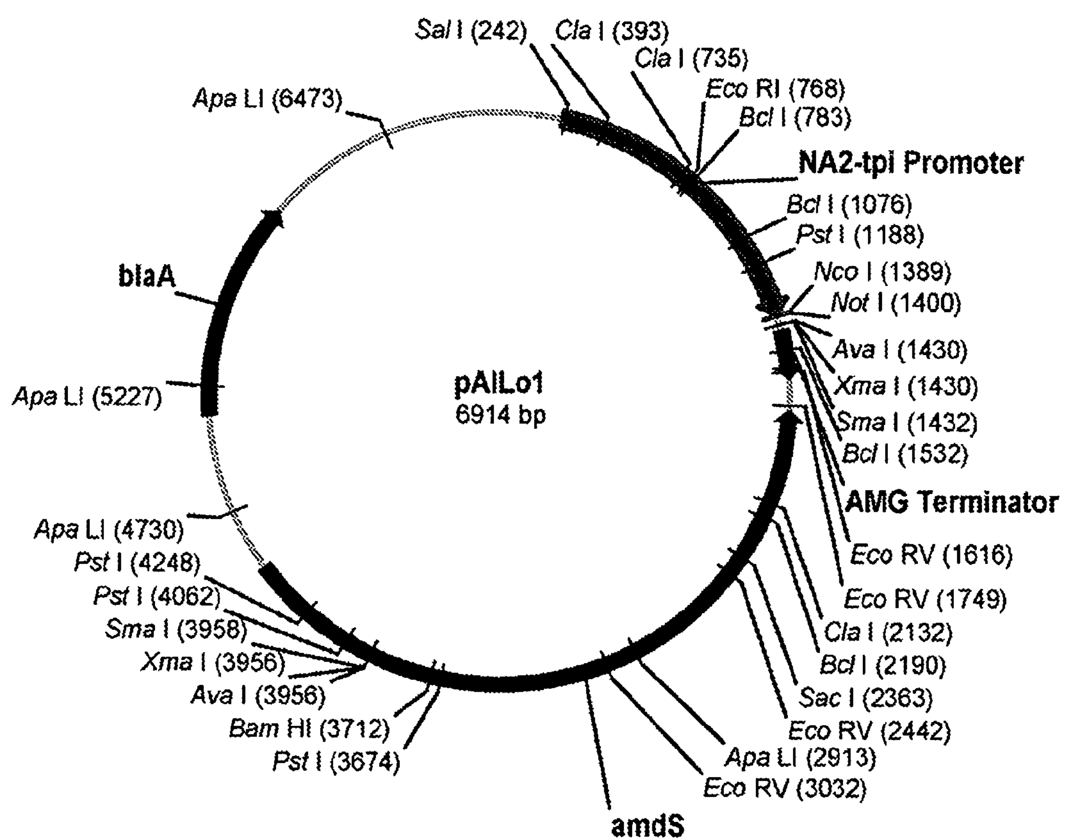
FIG. 5 shows a restriction map of pAILo1.

The last step in the modification of pBANe6 was the addition of a new Nco I restriction site at the beginning of the polylinker using a QuickChange™ Site-Directed Mutagenesis Kit and the following primers (underlined nucleotides represent the changed bases) to yield pAILo1 (FIG. 5).

```
Upper Primer to mutagenize the NA2-tpi promoter:
                                   (SEQ ID NO: 16)
5'-CTATATACACAACTGGATTTACCATGGGCCCGCGGCCGCAGA
TC-3'

Lower Primer to mutagenize the NA2-tpi promoter:
                                   (SEQ ID NO: 17)
5'-GATCTGCGGCCGCGGGCCCATGGTAAATCCAGTTGTGTATAT
AG-3'
```

Figure 6:
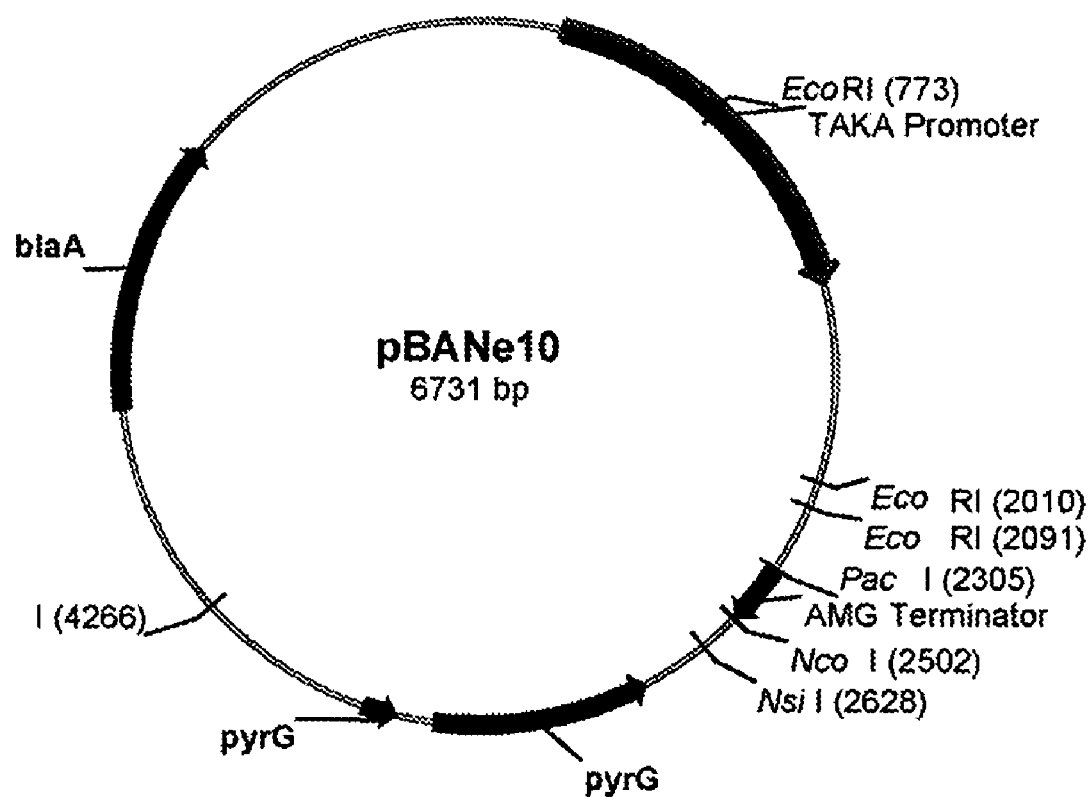
FIG. 6 shows a restriction map of pBANe10.
Figure 7:
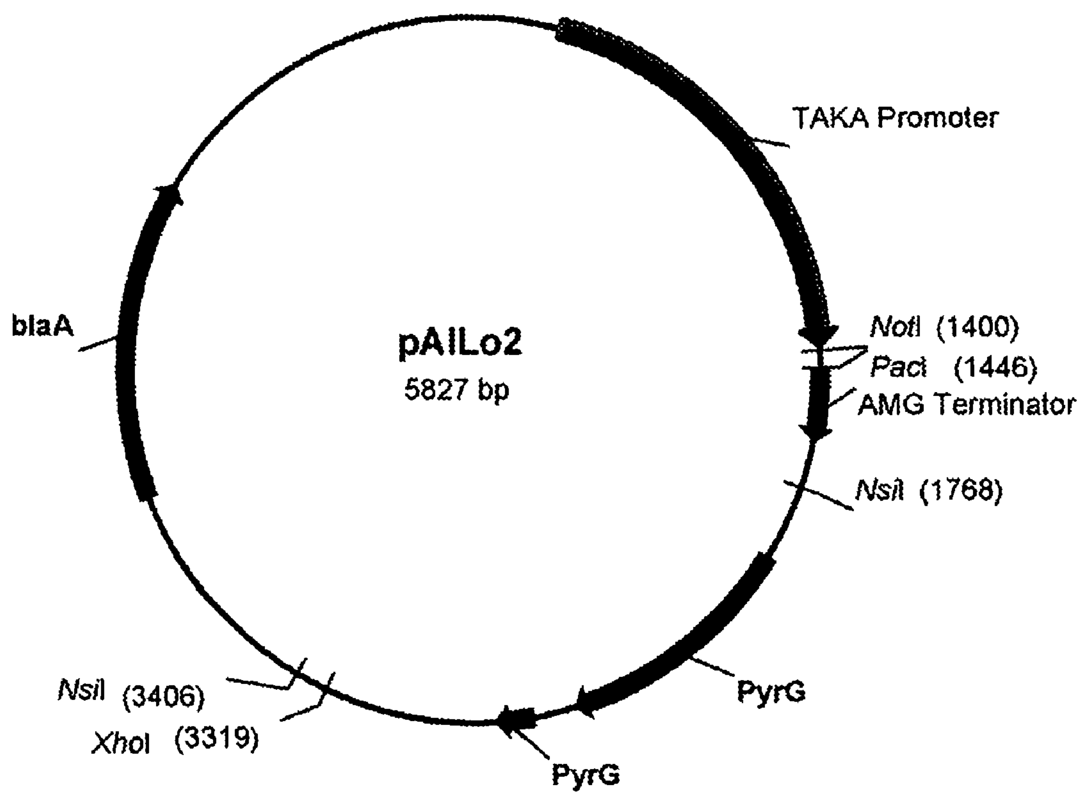
FIG. 7 shows a restriction map of pAILo2.

The amdS gene of pAILo1 was swapped with the *Aspergillus nidulans* pyrG gene. Plasmid pBANe10 (FIG. 6) was used as a source for the pyrG gene as a selection marker. Analysis of the sequence of pBANe10 showed that the pyrG marker was contained within an Nsi I restriction fragment and does not contain either Nco I or Pac I restriction sites. Since the amdS is also flanked by Nsi I restriction sites the strategy to switch the selection marker was a simple swap of Nsi I restriction fragments. Plasmid DNA from pAILo1 and pBANe10 were digested with the restriction enzyme Nsi I and the products purified by agarose gel electrophoresis. The Nsi I fragment from pBANe10 containing the pyrG gene was ligated to the backbone of pAILo1 to replace the original Nsi I DNA fragment containing the amdS gene. Recombinant clones were analyzed by restriction enzyme digestion to determine that they had the correct insert and also its orientation. A clone with the pyrG gene transcribed in the counterclockwise direction was selected. The new plasmid was designated pAILo2 (FIG. 7).

Example 8

Expression of *Thielavia terrestris* cel6b Endoglucanase Gene in *Aspergillus oryzae*

Two synthetic oligonucleotide primers, shown below, were designed to PCR amplify the full-length open reading frame from *Thielavia terrestris* PH47 encoding a CEL6B endoglucanase. An In-Fusion Cloning Kit (BD Biosciences, Palo Alto, Calif., USA) was used to clone the fragment directly into pAILo2.

```
In-Fusion Forward primer:
                                   (SEQ ID NO: 18)
5'-ACTGGATTACCATGAAGCTCTCGCAGTCG-3'

In-Fusion Reverse primer:
                                   (SEQ ID NO: 19)
5'-AGTCACCTCTAGTTAGAACGACGGCACGGC-3'
```

Bold letters represent coding sequence. The remaining sequence contains sequence identity compared with the insertion sites of pAILo2.

Fifty picomoles of each of the primers above were used in a PCR reaction containing 50 ng of pPH47 DNA, 1×Pfx Amplification Buffer (Invitrogen, Carlsbad, Calif., USA), 6 μl of 10 mM blend of dATP, dTTP, dGTP, and dCTP, 2.5 units of Platinum Pfx DNA Polymerase (Invitrogen, Carlsbad, Calif.), 1 μl of 50 mM MgSO4, and 5 μl of 10×pCRx Enhancer solution (Invitrogen, Carlsbad, Calif.) in a final volume of 50 μl. The amplification was performed in an Eppendorf Mastercycler 5333 (Eppendorf Scientific, Inc., Westbury, N.Y., USA) programmed for 1 cycle at 98° C. for 2 minutes; and 35 cycles each at 94° C. for 30 seconds, 65° C. for 30 seconds, and 68° C. for 1.5 minutes. After the 35 cycles, the reaction was incubated at 68° C. for 10 minutes and then cooled at 10° C. until further processed. A 1.5 kb PCR reaction product was isolated on a 0.8% GTG-agarose gel (Cambrex Bioproducts, East Rutherford, N.J., USA) using TAE buffer and 0.1 μg of ethidium bromide per ml. The DNA band was visualized with the aid of a Dark Reader™ (Clare Chemical Research, Dolores, Colo., USA) to avoid UV-induced mutations. The 1.5 kb DNA band was excised with a disposable razor blade and purified using a QIAquick Gel Extraction Kit (QIAGEN Inc., Valencia, Calif., USA) according to the manufacturer's instructions.

Figure 8:
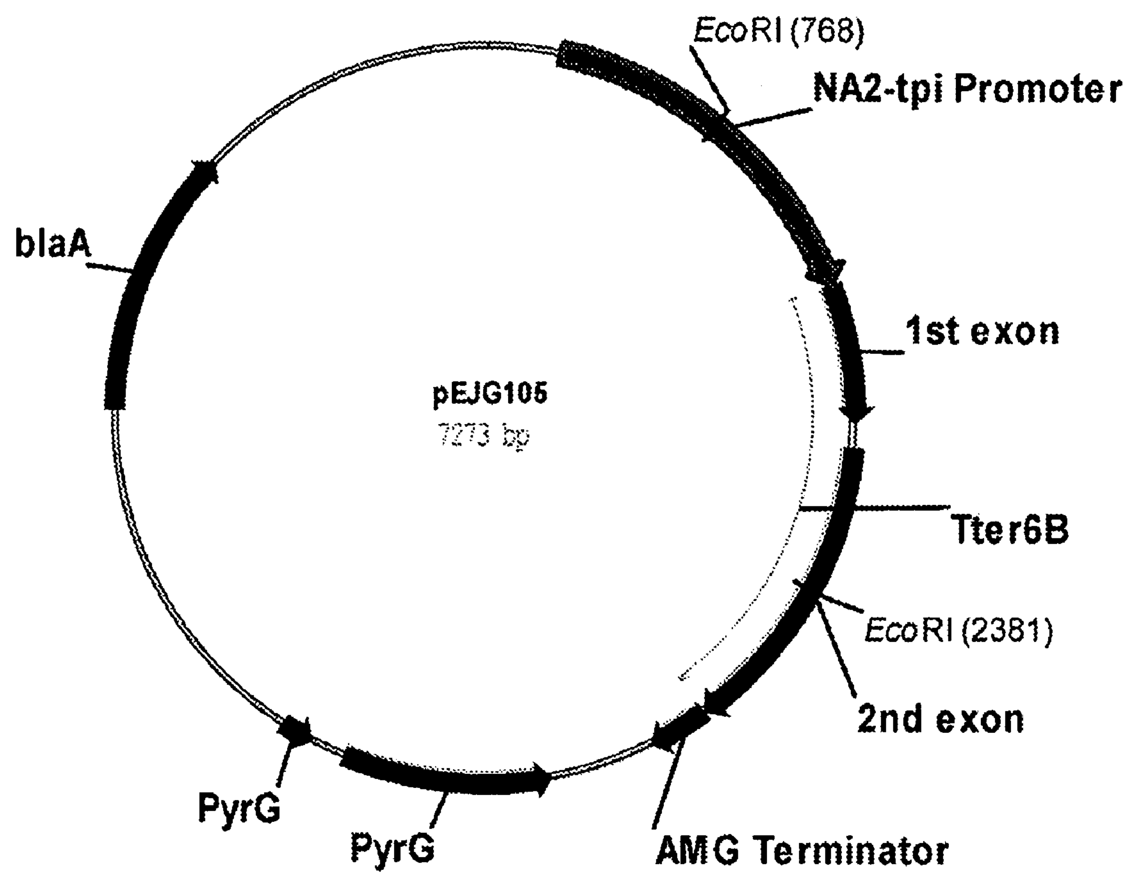
FIG. 8 shows a restriction map of pEJG105.

The vector pAILo2 was linearized by digestion with Nco I and Pac I (using conditions specified by the manufacturer). The fragment was purified by gel electrophoresis and a QIAquick Gel Extraction Kit as described above. Cloning of the purified PCR fragment into the linearized and purified pAILo2 vector was performed with an In-Fusion Cloning Kit. The reaction (20 μl) contained 1× In-Fusion Buffer (BD Biosciences, Palo Alto, Calif., USA), 1×BSA (BD Biosciences, Palo Alto, Calif., USA), 1 μl of In-Fusion enzyme (diluted 1:10) (BD Biosciences, Palo Alto, Calif., USA), 160 ng of pAILo2 digested with Nco I and Pac I, and 50 ng of the *Thielavia terrestris* cel6b purified PCR product. The reaction was incubated at room temperature for 30 minutes. A 1 μl sample of the reaction were used to transform *E. coli* XL10 SoloPac® Gold cells (Stratagene, La Jolla, Calif.) according to the manufacturer's instructions. After the recovery period, two 100 μl aliquots from the transformation reaction were plated onto 150 mm 2×YT plates supplemented with 100 μg of ampicillin per ml. The plates were incubated overnight at 37° C. A set of eight putative recombinant clones was selected at random from the selection plates and plasmid DNA was prepared from each one using a BioRobot 9600. Clones were analyzed by Eco RI restriction digest. Two clones that had the expected restriction digest pattern were then sequenced to confirm that there were no mutations in the cloned insert. One of the clones had the correct sequence and was selected and designated pEJG105 (FIG. 8).

*Aspergillus oryzae* JaI250 (WO 99/61651) protoplasts were prepared according to the method of Christensen et al., 1988, *Bio/Technology* 6: 1419-1422. Five micrograms of pEJG105 (as well as pAILo2 as a vector control) were used to transform *Aspergillus oryzae* JAL250 protoplasts.

The transformation of *Aspergillus oryzae* JaI250 with pEJG105 yielded about 100 transformants. Five transformants were isolated to individual PDA plates and incubated for five days at 34° C.

Confluent spore plates were washed with 5 ml of 0.01% Tween 80 and the spore suspension was used to inoculate 25 ml of MDU2BP medium in 125 ml glass shake flasks. Transformant cultures were incubated at 34° C. with constant shaking at 200 rpm. At day five post-inoculation, an aliquot of each culture was centrifuged at 12000×g. Five μl of each supernatant were mixed with an equal volume of 2× loading buffer (10% β-mercaptoethanol) and loaded onto a 1.5 mm 8%-16% Tris-Glycine SDS-PAGE gel and stained with Simply Blue SafeStain (Invitrogen, Carlsbad, Calif.). SDS-PAGE profiles of the culture broths showed that four out of five transformants had a new protein band of approximately 40 kDa. Transformant number 1 was selected for further studies and designated *Aspergillus oryzae* EJG105.

Example 9

Expression of *Thielavia terrestris* cel6c Endoglucanase Gene in *Aspergillus oryzae*

The *Thielavia terrestris* cel6c gene was excised from the pYES2.0 vector using Bam HI and Xba I, and ligated into the

Figure 9:
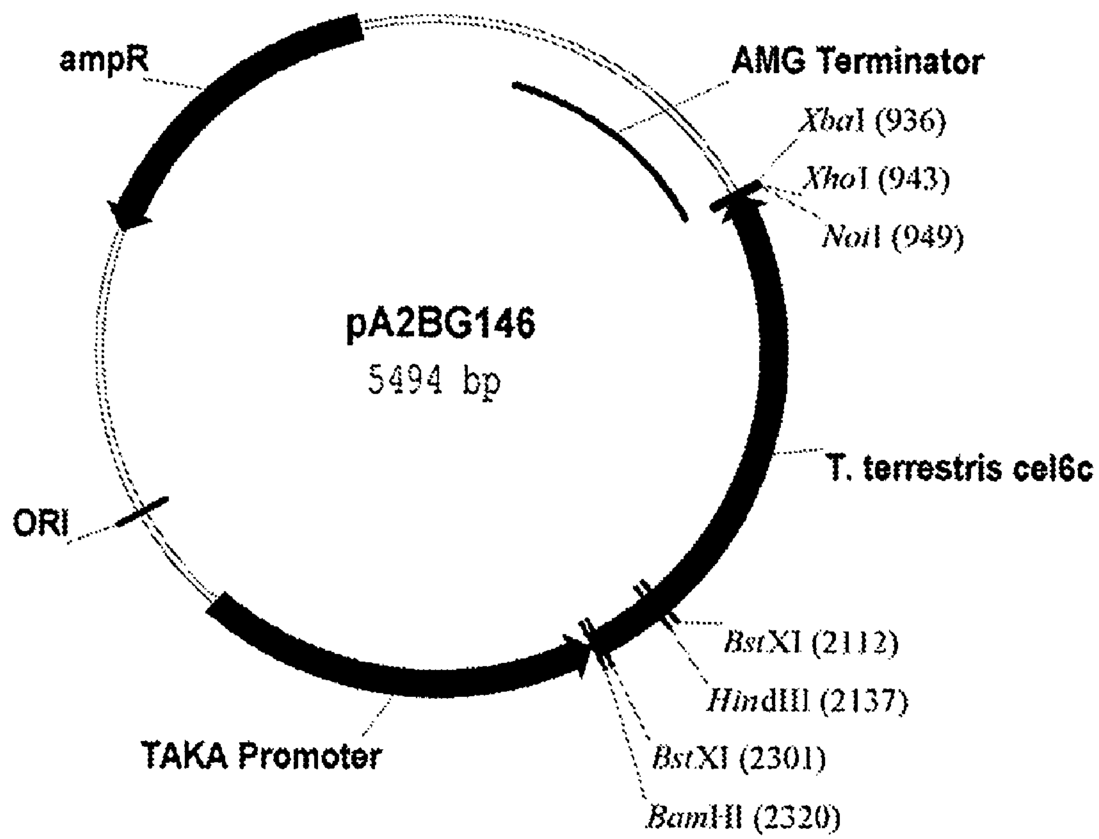
FIG. 9 shows a restriction map of pA2BG146.

*Aspergillus* expression vector pHD414 (EP 238 023, WO 93/11249) using standard methods (Sambrook et al., 1989, supra). The *Aspergillus* expression vector pHD414 is a derivative of p775 (EP 238 023). The resulting plasmid was designated pA2BG146 (FIG. 9).

Protoplasts of *Aspergillus oryzae* HowB104 were prepared as described in WO 95/02043. One hundred microliters of protoplast suspension was mixed with 5-25 μg of pA2BG146 in 10 μl of STC composed of 1.2 M sorbitol, 10 mM Tris-HCl, pH 7.5, 10 mM $CaCl_2$) and further mixed with 5-25 μg of p3SR2, an *Aspergillus nidulans* amdS gene carrying plasmid (Christensen et al., 1988, *Bio/Technology* 6: 1419-1422). The mixture was left at room temperature for 25 minutes. Two hundred microliters of 60% PEG 4000 (BDH, Poole, England) (polyethylene glycol, molecular weight 4,000), 10 mM $CaCl_2$, and 10 mM Tris-HCl pH 7.5 was added and gently mixed and finally 0.85 ml of the same solution was added and gently mixed. The mixture was left at room temperature for 25 minutes, centrifuged at 2,500×g for 15 minutes, and the pellet was resuspended in 2 ml of 1.2 M sorbitol. This sedimentation process was repeated, and the protoplasts were spread on COVE plates. After incubation for 4-7 days at 37° C. spores were picked and spread in order to isolate single colonies. This procedure was repeated and spores of a single colony after the second reisolation were stored.

Each of the transformants was inoculated in 10 ml of YPM medium. After 2-5 days of incubation at 30° C., 200 rpm, the supernatant was removed. Endoglucanase activity was identified by applying 20 μl of culture broth to 4 mm diameter holes punched out in a 0.1% AZCL HE cellulose SC-agar plate and incubation overnight at 30° C. Endoglucanase activity was then identified by a blue halo around a colony. Several transformant broths had endoglucanase activity that was significantly greater than broth from an untransformed *Aspergillus oryzae* background control, which demonstrated efficient expression of the CEL6C endoglucanase from *Thielavia terrestris* NRRL 8126 in *Aspergillus oryzae.*

Example 10

Large Shake Flask Cultures of *Aspergillus oryzae* JaI250 Containing cel6b Gene

*Aspergillus oryzae* JaI250 containing pEJG105 spores were spread onto a PDA plate and incubated for five days at 34° C. The confluent spore plate was washed twice with 5 ml of 0.01% Tween 80 to maximize the number of spores collected. The spore suspension was then used to inoculate 500 ml of MDU2BP medium in a two-liter Fernbach flask. The culture was incubated at 34° C. with constant shaking (200 rpm). At day five post inoculum, the culture broth was collected by filtration on a 500 milliliter, 75 mm Nylon filter unit with a pore size of 0.45 μm with a glass-fiber pre-filter (Nalgene Nunc International, Rochester, N.Y., USA). A 5 μl sample of the broth was analyzed by SDS-PAGE as described in Example 9 to confirm that the protein pattern was the same as the one obtained before. The broth was shown to contain a 40 kDa protein band.

Deposit of Biological Material

The following biological material have been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| *E. coli* PaHa47 (pPH47) | NRRL B-30898 | Feb. 23, 2006 |
| *E. coli* (pCIBG146) | NRRL B-30901 | Feb. 23, 2006 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having endoglucanase activity, selected from the group consisting of:

(a) a polypeptide comprising an amino acid sequence having at least 90% identity with the mature polypeptide of SEQ ID NO: 2 or the mature polypeptide of SEQ ID NO: 4;

(b) a polypeptide encoded by a polynucleotide which hybridizes under at least high stringency conditions with (i) the mature polypeptide coding sequence of SEQ ID NO: 1 or the mature polypeptide coding sequence of SEQ ID NO: 3, (ii) the cDNA sequence of the mature polypeptide coding sequence of SEQ ID NO: 1 or the qenomic DNA sequence of the mature polypeptide coding sequence of SEQ ID NO: 3, or (iii) the full-length complementary strand of (i) or (ii), wherein high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 65° C.; and (c) a polypeptide encoded by a polynucleotide comprising a nucleotide sequence having at least 90% identity with the mature polypeptide coding sequence of SEQ ID NO: 1 or the mature polypeptide coding sequence of SEQ ID NO: 3.

2. The polypeptide of claim 1, which comprises an amino acid sequence having at least 90% identity with the mature polypeptide of SEQ ID NO: 2 or the mature polypeptide of SEQ ID NO: 4.

3. The polypeptide of claim 2, which comprises an amino acid sequence having at least 95% identity with the mature polypeptide of SEQ ID NO: 2 or the mature polypeptide of SEQ ID NO: 4.

4. The polypeptide of claim 3, which comprises an amino acid sequence having at least 97% identity with the mature polypeptide of SEQ ID NO: 2 or the mature polypeptide of SEQ ID NO: 4.

5. The polypeptide of claim 1, which is encoded by a polynucleotide comprising a nucleotide sequence having at least 90% identity with the mature polypeptide coding sequence of SEQ ID NO: 1 or the mature polypeptide of SEQ ID NO: 3.

6. The polypeptide of claim 5, which is encoded by a polynucleotide comprising a nucleotide sequence having at least 95% identity with the mature polypeptide coding sequence of SEQ ID NO: 1 or the mature polypeptide of SEQ ID NO: 3.

7. The polypeptide of claim 6, which is encoded by a polynucleotide comprising a nucleotide sequence having at least 97% identity with the mature polypeptide coding sequence of SEQ ID NO: 1 or the mature polypeptide of SEQ ID NO: 3.

8. The polypeptide of claim 1, which is encoded by a polynucleotide that hybridizes under at least high stringency conditions with (i) the mature polypeptide coding sequence of SEQ ID NO: 1 or the mature polypeptide coding sequence of SEQ ID NO: 3, (ii) the cDNA sequence of the mature polypeptide coding sequence of SEQ ID NO: 1 or the genomic DNA sequence of the mature polypeptide coding sequence of SEQ ID NO: 3, or (iii) the full-length complementary strand of (i) or (ii), wherein high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 65° C.

9. The polypeptide of claim 8, which is encoded by a polynucleotide that hybridizes under at least very high stringency conditions with (i) the mature polypeptide coding sequence of SEQ ID NO: 1 or the mature polypeptide coding sequence of SEQ ID NO: 3, (ii) the cDNA sequence of the mature polypeptide coding sequence of SEQ ID NO: 1 or the genomic DNA sequence of the mature polypeptide coding sequence of SEQ ID NO: 3, or (iii) the full-length complementary strand of (i) or (ii), wherein very high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 70° C.

10. The polypeptide of claim 1, which comprises or consists of the amino acid sequence of SEQ ID NO: 2 or SEQ ID NO: 4.

11. The polypeptide of claim 1, which comprises or consists of the mature polypeptide of SEQ ID NO: 2 or the mature polypeptide of SEQ ID NO: 4.

12. The polypeptide of claim 1, which is encoded by the polynucleotide contained in plasmid pPH47 which is contained in *E. coli* NRRL B-30898 or plasmid pCIBG146 which is contained in *E. coli* NRRL B-30901.

13. A method of degrading or converting a cellulosic material, comprising: treating the cellulosic material with a composition comprising an effective amount of a polypeptide having endoglucanase activity of claim 1.

14. The method of claim 13, wherein the composition further comprises an effective amount of one or more enzymes selected from the group consisting of an endo-1,4-beta-glucanase, a exo-1,4-beta-D-glucanase, a beta-D-glucosidase, a hemicellulase, an esterase, a protease, a laccase, and a peroxidase.

15. The method of claim 13, which is a simultaneous saccharification and fermentation process (SSF); or in a hybrid hydrolysis and fermentation process (HHF).

16. The method of claim 13, further comprising recovering the degraded or converted cellulosic material.

17. A method of producing a fermentation product, comprising: (a) saccharifying a cellulosic material with a composition comprising an effective amount of the polypeptide having endoglucanase activity of claim 1, (b) fermenting the saccharified cellulosic material of step (a) with one or more fermentating microorganisms to produce the fermentation product; and (c) recovering the fermentation product from the fermentation.

18. The method of claim 17, wherein the composition further comprises an effective amount of one or more enzymes selected from the group consisting of an endo-1,4-beta-glucanase, a exo-1,4-beta-D-glucanase, a beta-D-glucosidase, a hemicellulase, an esterase, a protease, a laccase, and a peroxidase.

19. The method of claim 17, wherein steps (a) and (b) are performed simultaneously in a simultaneous saccharification and fermentation.

20. The method of claim 17, wherein the fermentation product is an alcohol, an organic acid, a ketone, an amino acid, or a gas.

* * * * *